United States Patent
Deaton et al.

(10) Patent No.: US 12,194,142 B2
(45) Date of Patent: *Jan. 14, 2025

(54) BACILLUS SUBTILIS CONTAINING COMPOSITION FOR TREATMENT OF GASTROINTESTINAL IRREGULARITY

(71) Applicant: Deerland Enzymes, Inc., Kennesaw, GA (US)

(72) Inventors: John Deaton, Kennesaw, GA (US); Ana Maria Cuentas, Woodstock, GA (US)

(73) Assignee: Deerland Enzymes, Inc., Kennesaw, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/353,418

(22) Filed: Jun. 21, 2021

(65) Prior Publication Data

US 2021/0315808 A1 Oct. 14, 2021

Related U.S. Application Data

(63) Continuation-in-part of application No. 16/141,569, filed on Sep. 25, 2018, now abandoned.

(60) Provisional application No. 62/562,859, filed on Sep. 25, 2017.

(51) Int. Cl.
| | |
|---|---|
| A61K 35/742 | (2015.01) |
| A61K 9/00 | (2006.01) |
| A61P 1/14 | (2006.01) |
| A61B 10/00 | (2006.01) |
| A61K 35/00 | (2006.01) |

(52) U.S. Cl.
CPC .......... *A61K 9/0053* (2013.01); *A61K 35/742* (2013.01); *A61P 1/14* (2018.01); *A61B 10/0038* (2013.01); *A61K 2035/115* (2013.01)

(58) Field of Classification Search
CPC ................ A61K 9/0053; A61K 35/742; A61K 2035/115; A61K 9/4866; A61P 1/14; A61P 1/12; A61B 10/0038
See application file for complete search history.

(56) References Cited

U.S. PATENT DOCUMENTS

| | | | |
|---|---|---|---|
| 6,461,607 | B1 | 10/2002 | Farmer |
| 9,247,757 | B2 | 2/2016 | Schmidt et al. |
| 9,457,054 | B2 | 10/2016 | Schmidt et al. |
| 2013/0344045 | A1* | 12/2013 | Faure ............... A23L 33/16 424/93.45 |
| 2016/0100607 | A1 | 4/2016 | Schmidt et al. |

OTHER PUBLICATIONS

Labellarte, G. et al. Tolerance and Efficacy of a Probiotic Supplement Delivered in Capsule Form, 2015, The FASEB Journal, 29(1), Abstract No. 924.33 (Year: 2015).*
Labellarte, G. Tolerance and efficacy of a probiotic delivered in capsule form, 2014, University of Wisconsin-La Crosse, http://digital.library.wisc.edu/1793/71760 (Year: 2014).*
National Products Insider, Deerland Enzymes Launches Probiotic Strain DE111, 2014, https://www.naturalproductsinsider.com/digestive-health/deerland-enzymes-launches-probiotic-strain-de111 (Year: 2014).*
Lee, C. H. et al. Addition of probiotics to antibiotics improves the clinical course of pneumonia in young people without comorbidities: a randomized controlled trial, Jan. 13, 2021, Nature Scientific Reports, 11(926): 1-9 (Year: 2021).*
M.R. Blake, et al., "Validity and reliability of the Bristol Stool Form Scale in healthy adults and patients with diarrhoea-predominant irritable bowel syndrome," 44 Alimentary Pharmacology & Therapeutics 693 (2016).
Panuwan Chantawannakul, et al., "Characterization of proteases of Bacillus subtilis strain 38 isolated from traditionally fermented soybean in Northern Ireland," 28 Scienceasia 241 (2002).
Y. Inatsu, et al., "Characterization of Bacillus subtilis strains in Thua nao, a traditional fermented soybean food in northern Thailand," 43 Letters in Applied Microbiology 237 (2006).
Marie Lefevre, et al., "Probiotic strain Bacillus subtilis CU1 stimulates immune system of elderly during common infectious disease period: a randomized, double-blind placebo-controlled study," 12(24) Immunity & Ageing (2015).
Jorge Olmos & J. Paniagua-Michel, "Bacillus subtilis—A Potential Bacterium to Formulate Functional Feeds for Aquaculture," 6 J. Microbial & Biochemical Tech. 361 (2014).
Kazunobu Omura, et al., "A Newly Derived Protein From Bacillus subtilis natto With Both Antithrombotic and Fibrinolytic Effects," 99 J. Pharmacological Scis. 247 (2005).
Junjie Qin, et al., "A human gut microbial gene catalogue established by metagenomic sequencing," 464 Nature 59 (2010).
G.M. Lebellarte, "Tolerance and Efficacy of a Probiotic Supplement Delivered in Capsule Form," Thesis Submitted in Partial Fulfillment of the Requirements for the Degree of Master of Science in Biology, College of Science and Health Biology/Physiology, http://digital.library.wisc.edu/1793/71760 (University of Wisconsin—La Crosse, Dec. 2014).
Natural Products Insider, "Deerland Enzymes Launches Probiotic Strain DE111," https://www.naturalproductsinsider.com/digestive-health/deerland-enzymes-launches-probiotic-strain-de111 (Oct. 13, 2014).
Rooney, Alejandro P. et al., "Phylogeny and molecular taxonomy of the Bacillus subtilis species complex and description of Bacillus subsp. inaquosorum subsp. nov."; International Journal of Systematic and Evolutionary Microbiology (2009), 59, 2429-2436.

(Continued)

*Primary Examiner* — Louise W Humphrey
*Assistant Examiner* — Anjali Ajit Hirani
(74) *Attorney, Agent, or Firm* — Amin Wasserman Gurnani LLP; George M. Carrera, Jr.

(57) ABSTRACT

The present invention relates to methods of treating gastrointestinal irregularity, as well as promoting, maintaining, and restoring gastrointestinal regularity, and maintaining healthy gut microflora in an individual. The present invention relates to methods comprising orally administering to an individual a *Bacillus subtilis* composition wherein the individual's gastrointestinal irregularity is treated, and/or the individual's gastrointestinal regularity and/or healthy gut microflora is promoted, maintained, and/or restored.

29 Claims, 2 Drawing Sheets

(56) References Cited

OTHER PUBLICATIONS

Arce, DA, et al. "Evaluation of constipation", Am Fam Physician. Jun. 1, 2002;65(11):2283-90.
Park, MN, et al. "The relationship between primary headache and constipation in children and adolescents", Korean J Pediatr. Feb. 2015;58(2):60-3.

* cited by examiner

BACILLUS SUBTILIS CONTAINING COMPOSITION FOR TREATMENT OF GASTROINTESTINAL IRREGULARITY

This application is a Continuation-in-Part of U.S. application Ser. No. 16/141,569, filed on Sep. 25, 2018, which claims the benefit of U.S. Provisional Application No. 62/562,859, filed on Sep. 25, 2017. The disclosures of the prior applications are each incorporated herein by reference in their entireties for all purposes.

TECHNICAL FIELD OF THE INVENTION

The present disclosure relates to methods of treating gastrointestinal irregularity, maintaining gastrointestinal regularity, promoting gastrointestinal regularity, restoring gastrointestinal regularity, and/or maintaining healthy gut microflora, with *Bacillus subtilis*-containing composition(s). The *Bacillus subtilis*-containing composition(s) can be used as probiotic supplementation of the gastrointestinal microflora.

BACKGROUND

People who have at least one bowel movement per day and pass good textured feces (not too hard or soft) are considered to have "normal" bowel function. However, occasional constipation and/or diarrhea can be a burdensome gastrointestinal issue that occurs in many individuals and whose treatment remains challenging.

Further, technological progress in the food industry (heat treatment, cooling, freezing, etc.) has resulted in a dramatic decrease of consumption of food-borne microbes and has coincided with an increased number of disorders including inflammatory bowel disease and atopic disorders such as asthma and food allergies.

The term "probiotics" can refer to live microorganisms which when administered in adequate amounts confer a health benefit on the host. See, e.g., FAO/WHO, *Health and Nutrition Properties of Probiotics in Food including Powder Milk with Live Lactic Acid Bacteria Report of a Joint FAO/WHO Expert Consultation on Evaluation of Health and Nutritional Properties of Probiotics in Food including Powder Milk with Live Lactic Acid Bacteria*, Report 2001, Cordoba, Argentina, 1-4 Oct. 2001, Report No. 0254-4725, incorporated by reference herein in its entirety. *Lactobacillus* and *Bifidobacterium* are the most commonly used bacterial probiotics. Foods and food additives containing probiotics may support the restoration of the healthy balance of the gut microflora.

Further, probiotic supplementation of the intestinal flora may promote healthy intestinal homeostasis. There is some evidence that *Bacillus subtilis* might be a part of the normal gut flora of humans. As a component of the human microbiome, *Bacillus subtilis* may potentially have the ability to promote gastrointestinal health, including helping its host in digestion, making *Bacillus subtilis* a good candidate for probiotic compositions.

Several studies have revealed that some probiotic products in the market have deficiencies in the viability of probiotic strain(s), especially in products containing bifidobacteria. This may be due to storage conditions, manufacturing, or food technology setbacks, such as inappropriate packaging materials that could affect probiotic stability through variations in oxygen permeability. In the past two decades, there has been renewed interest in the study of the nutritional and therapeutic aspects of probiotic products.

It is widely accepted that probiotics may exert positive influence on the host through modulation of the endogenous ecosystem and stimulation of immune system as well as maintaining a healthy intestinal microflora. However, research suggests that health benefits are strain-specific and vary by amount ingested and duration administered. Further, probiotic applications are limited because these bacteria are likely to be in a stressed state when they reach the colon due to exposure to diverse barriers in the host such as gastric acid and bile acids. Commercial probiotics should be able to recover and compete with established microflora in the colon to provide colonization and benefits for the host, but such products can often fail to achieve the desired benefits.

Accordingly, there exists a need for methods of treating gastrointestinal irregularity using a *Bacillus subtilis*-containing composition.

SUMMARY OF THE INVENTION

In an embodiment, the present disclosure relates to a method of treating gastrointestinal irregularity in an individual, wherein the individual has at least one 24-hour episode per month of bowel movements measuring 1 or 2 on the Bristol Stool Scale.

In an embodiment, a method of treating gastrointestinal irregularity in an individual, wherein the individual has at least one 24-hour episode per month of bowel movements measuring 1 or 2 on the Bristol Stool Scale, can include the steps of:
(a) administering orally to the individual a composition comprising *Bacillus subtilis* in a dose of from about $1 \cdot 10^8$ CFU per day to about $1 \cdot 10^{11}$ CFU per day for at least 15 days;
wherein the frequency of the individual's 24-hour episodes per month of bowel movements measuring 1 or 2 on the Bristol Stool Scale decreases.

The process described herein effects a treatment of gastrointestinal irregularity in an individual.

In another embodiment, the administering step of the method of treating gastrointestinal irregularity in an individual is performed for at least 30 days.

In yet another embodiment, the administering step of the method of treating gastrointestinal irregularity in an individual is performed for at least 60 days.

In yet another embodiment, the administering step of the method of treating gastrointestinal irregularity in an individual is performed for at least 90 days.

In yet another embodiment, the composition comprises *Bacillus subtilis* in a dose of about $1 \cdot 10^9$ CFU per day.

In yet another embodiment, a method of treating gastrointestinal irregularity in an individual, wherein the individual has at least one 24-hour episode per month of bowel movements measuring 1 or 2 on the Bristol Stool Scale, can include the steps of:
(a) administering orally to the individual a composition comprising *Bacillus subtilis* in a dose of from about $1 \cdot 10^8$ CFU per day to about $1 \cdot 10^{11}$ CFU per day for at least 15 days; (b) measuring the individual's bowel movements according to the Bristol Stool Scale;
wherein steps (a) and (b) are repeated at least until the frequency of the individual's 24-hour episodes per month of bowel movements measuring 1 or 2 on the Bristol Stool Scale decreases.

In yet another embodiment, a method of treating gastrointestinal irregularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of from about $1 \cdot 10^8$ CFU per day to about $1 \cdot 10''$ CFU per day for at least 15 days;
  wherein the frequency of the individual's 24-hour episodes per month of bowel movements measuring 6 or 7 on the Bristol Stool Scale decreases.

The process described herein effects a treatment of gastrointestinal irregularity in an individual.

In yet another embodiment, the administering step of the method of treating gastrointestinal irregularity in an individual is performed for at least 30 days.

In yet another embodiment, the administering step of the method of treating gastrointestinal irregularity in an individual is performed for at least 60 days.

In yet another embodiment, the administering step of the method of treating gastrointestinal irregularity in an individual is performed for at least 90 days.

In yet another embodiment, the composition comprises *Bacillus subtilis* in a dose of about $1 \cdot 10^9$ CFU per day.

In yet another embodiment, a method of treating gastrointestinal irregularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days; (b) measuring the individual's bowel movements according to the Bristol Stool Scale;
  wherein steps (a) and (b) are repeated at least until the frequency of the individual's 24-hour episodes per month of bowel movements measuring 6 or 7 on the Bristol Stool Scale decreases.

In an embodiment, the present disclosure relates to a method of maintaining gastrointestinal regularity in an individual.

In an embodiment, a method of maintaining gastrointestinal regularity in an individual can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days;
  wherein the frequency of the individual's 24-hour episodes per month of bowel movements measuring 1 or 2 or 6 or 7 on the Bristol Stool Scale does not increase during the at least 15 days.

The process described herein effects maintenance of gastrointestinal regularity in an individual.

In another embodiment, the administering step of the method of maintaining gastrointestinal regularity in an individual is performed for at least 30 days.

In yet another embodiment, the administering step of the method of maintaining gastrointestinal regularity in an individual is performed for at least 60 days.

In yet another embodiment, the administering step of the method of maintaining gastrointestinal regularity in an individual is performed for at least 90 days.

In yet another embodiment, the composition comprises *Bacillus subtilis* in a dose of about $1 \cdot 10^9$ CFU per day.

In an embodiment, the present disclosure relates to a method of promoting gastrointestinal regularity in an individual.

In an embodiment, a method of promoting gastrointestinal regularity in an individual can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days;
  wherein the frequency of the individual's 24-hour episodes per month of bowel movements measuring from 3 to 5 on the Bristol Stool Scale increases.

The process described herein effects promotion of gastrointestinal regularity in an individual.

In another embodiment, the administering step of the method of promoting gastrointestinal regularity is performed for at least 30 days.

In yet another embodiment, the administering step of the method of promoting gastrointestinal regularity is performed for at least 60 days.

In yet another embodiment, the administering step of the method of promoting gastrointestinal regularity is performed for at least 90 days.

In yet another embodiment, the composition comprises *Bacillus subtilis* in a dose of about $1 \cdot 10^9$ CFU per day.

In yet another embodiment, a method of promoting gastrointestinal regularity in an individual can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days; (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

In an embodiment, the present disclosure relates to a method of restoring gastrointestinal regularity in an individual.

In an embodiment, a method of restoring gastrointestinal regularity in an individual, wherein the individual has at least one 24-hour episode per month of bowel movements measuring 1 or 2 or 6 or 7 on the Bristol Stool Scale, can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days;
  wherein the frequency of 24-hour periods of the individual's bowel movements measuring from 3 to 5 on the Bristol Stool Scale increases.

The process described herein effects restoration of gastrointestinal regularity in an individual.

In another embodiment, the administering step of the method of restoring gastrointestinal regularity is performed for at least 30 days.

In yet another embodiment, the administering step of the method of restoring gastrointestinal regularity is performed for at least 60 days.

In yet another embodiment, the administering step of the method of restoring gastrointestinal regularity is performed for at least 90 days.

In yet another embodiment, the composition comprises *Bacillus subtilis* in a dose of about $1 \cdot 10^9$ CFU per day.

In yet another embodiment, a method of restoring gastrointestinal regularity in an individual can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days; (b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

DETAILED DESCRIPTION

Figure 1:
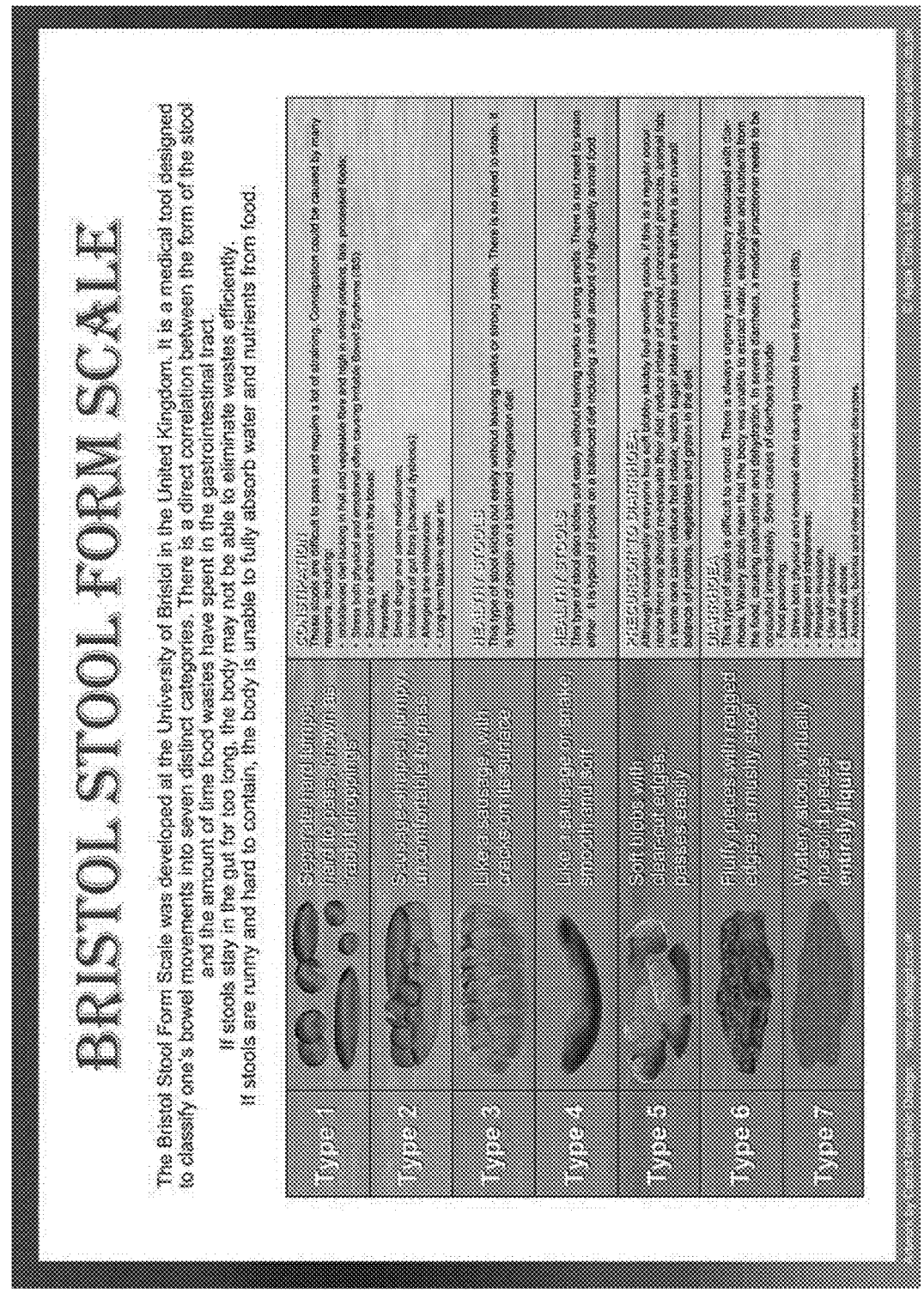
FIG. 1 depicts the Bristol Stool Form Scale used in the study reported herein for participant evaluation of participant-reported bowel movements ("BMs").

In certain embodiments, the present invention relates to a novel use of Bacillus subtilis strain DE111® (Bacillus subtilis subspecies inaquosorum having Accession No. NRRL B-67989) and/or its metabolites that are effective to treat gastrointestinal irregularity, maintain gastrointestinal regularity, promote gastrointestinal regularity, restore gastrointestinal regularity, and/or maintain healthy gut microflora, as probiotics. In a particular embodiment, a Bacillus subtilis (B. subtilis) containing composition is used for treatment of gastrointestinal ("GI") irregularity and like conditions, for example, constipation and diarrhea, in a human or animal subject.

Embodiments of the present invention encompass methods of treating gastrointestinal irregularity, maintaining gastrointestinal regularity, promoting gastrointestinal regularity, restoring gastrointestinal regularity, and/or maintaining healthy gut microflora, by administering to a patient in need thereof a composition comprising (i) Bacillus subtilis DE111® (Bacillus subtilis subspecies inaquosorum having Accession No. NRRL B-67989), (ii) mutants of Bacillus subtilis DE111®, (iii) cell-free preparations of (i) or (ii), or (iv) metabolites of (i) or (ii).

As used herein, the term "GI tract" refers to the gastrointestinal tract or pathway in individuals including humans, mammals, and other domesticated animals. The GI tract includes at least the stomach and small intestine, and for test purposes, can include the alimentary canal. Passage or transit through, or residence in, the GI tract is understood to proceed starting from the mouth (via chewing, mastication, liquid delivery, or swallowing, for example), which is followed by ingestion to the stomach, and subsequently to the intestines. Colonization, growth, and maintenance of probiotic bacteria can occur in the GI tract, particularly in the intestines.

Currently, there is a rapid growth of interest in probiotics to promote better health and well-being, which shows a substantial promise to expand the food industry into new fields. Strains from genera of Lactobacillus and Bifidobacterium species, both of which are indigenous to the human intestine, are predominantly selected for use although some other species have also been used as well. Probiotics, also termed as functional foods, are commonly found in dairy products such as yogurt and cultured milk drinks or even in the form of health supplements.

Useful bacterial strains for probiotic compositions can include, but are not limited to, Lactobacillus plantarum, Bifidobacterium bifidum, Bifidobacterium lactis, Lactobacillus rhamnosus, Lactobacillus acidophilus, Bacillus coagulans, Bacillus subtilis, and the like.

The Bacillus species are rod-shaped, spore-forming, aerobic, gram-positive bacteria that are ubiquitous in nature. There is some evidence that Bacillus subtilis might be a part of the normal gut flora of humans. Some human intestinal biopsy samples have shown that Bacillus subtilis does populate the gut in humans as normal human intestinal flora. See, e.g., Junjie Qin, et al., A human gut microbial gene catalogue established by metagenomics sequencing, 464 NATURE 59 (2010), incorporated by reference herein in its entirety.

The Lactobacillus genus is extremely diverse and expanding every year. With over 230 species, it has grown into one of the biggest genera in the bacterial taxonomy. As the genus has exceeded the acceptable "normal diversity," renaming and re-classification is inevitable wherein the genus Lactobacillus may be split into most likely twelve new genera. Many traditional "probiotic" species with substantiated industrial importance and starter cultures may no longer eventually be called "Lactobacillus." Hence, a substantial communication challenge looms ahead to reduce the inevitable confusion regarding the "old commercial" and "correct scientific" nomenclature. Once the International Committee on Systematics of Prokaryotes publishes new nomenclature in their official journal, the INTERNATIONAL JOURNAL OF SYSTEMATIC AND EVOLUTIONARY MICROBIOLOGY, the changes are valid and official. The manuscript that will be submitted for publication outlining the new nomenclature of the Lactobacillus genus will likely be ready for submission in by the end of 2018. Meanwhile, there is a taxonomic subcommittee meeting in September 2018 to discuss the nomenclature changes and an (invite-only) expert LABIP workshop in October 2018 that will evaluate the science while considering the consequences for regulations, legal/IP, and industry.

Bacillus subtilis has been used abundantly in traditional ethnic food processing, for example, in East Asia. Natto, in particular, is a cheese-like food, processed by inoculating soaked and steamed soybeans with live Bacillus from rice straw. Bacillus subtilis is the main component in the alkaline fermentation of soybeans without salt. Protease and amylase produced by the bacteria decompose protein and insoluble sugar in the raw soybeans, thus increasing the nutritional value as well as the availability of the soybean foods. See, e.g., K. H. Steinkraus, Fermentations in world food processing, 1 COMPREHENSIVE REVIEWS IN FOOD SCI. & FOOD SAFETY 23 (2000), incorporated by reference herein in its entirety. Fermentation not only enriches the nutrients but also enhances the health-promoting effectiveness of soybeans. Compared with nonfermented soybeans, fermented soybeans contain significantly more isoflavone genestein, a chemopreventive agent against cancer. See, e.g., M. Fukutake, et al., Quantification of genistein and genistin in soybeans and soybean products, 34 FOOD & CHEMICAL TOXICOLOGY 457 (1996); M. J. Messina, et al., Soy intake and cancer risk: a review of the in vitro and in vivo data, 21 NUTRITION & CANCER 113 (1994); each of which is incorporated by reference herein in its entirety.

Gamma-polyglutamic acid ("PGA") is the main component of a sticky material in Japanese fermented soybeans (natto) and increases soluble calcium in the small intestine and thereby increases the efficacy of calcium absorption. See, e.g., H. Tanimoto, et al., Natto mucilage containing poly-gamma-glutamic acid increases soluble calcium in the rat small intestine, 65 BIOSCIENCE, BIOTECHNOLOGY, & BIOCHEMISTRY 516 (2001), incorporated by reference herein in its entirety. PGA also acts as dietary fiber to reduce the cholesterol level in serum. See, e.g., K. Tsuji & E. Tsuji, *Effect of Natto-feeding on cholesterol level of rats*, 44 JAPAN J. NUTRITION & DIETETICS 41 (1986), incorporated by reference herein in its entirety. Natto extract exhibits antioxidative activity, anti-tumor activity, and angiotensin-I converting enzyme inhibitory activity. See, e.g., H. Esaki, et al., *Antioxidative activity of Natto*, 37 J. JAPANESE SOC'Y FOR FOOD SCI. & TECH. 474 (1990); C. Takahashi, et al., *Possible anti-tumor-promoting activity of components in Japanese soybean fermented food, Natto: effect on gap functional intercellular communication*, 16 CARCINOGENESIS 471 (1995); A. Okamoto, et al., *Angiotensin I converting enzyme inhibitory activity of various fermented foods*, 59 BIOSCIENCE, BIOTECHNOLOGY, & BIOCHEMISTRY 1147 (1995); each of which is incorporated by reference herein in its entirety.

Certain strains of *Bacillus subtilis* isolated from natto produce subtilisin NAT (formerly designated BSP, or nattokinase), which exhibits strong fibrinolytic activity. See, e.g., H. Sumi, et al., *Enhancement of the fibrinolytic activity in plasma by oral administration of natto kinase*, 84 ACTA HAEMATOLOGICA 139 (1990); M. Fujita, et al., *Thrombolytic effect of nattokinase on a chemically induced thrombosis model in rat*, 18 BIOLOGICAL & PHARM. BULLETIN 1387 (1995); each of which is incorporated by reference herein in its entirety. Subtilisin NAT-producing *Bacillus* strains have been isolated not only from natto but also from fermented soybean foods from Korea, Taiwan, and China. Dietary supplementation with natto suppresses intimal thickening and modulates the lysis of mural thrombi. See, e.g., Y. Suzuki, et al., *Dietary supplementation with fermented soybeans suppresses intimal thickening*, 19 NUTRITION 261 (2003); Y. Suzuki, et al., *Dietary supplementation of fermented soybean, natto, suppresses intimal ticking and modulates the lysis of mural thrombi after endothelial injury in rat femoral artery*, 73 LIFE SCIS. 1289 (2003); each of which is incorporated by reference herein in its entirety. Both the decrease in thrombus count and plasma euglobulin and the increase in tissue plasminogen activator are caused by oral intake of *Bacillus subtilis* BN-1 strain. See, e.g., H. Sumi, et al., *Natto Bacillus as an oral fibrinolytic agent: nattokinase activity and the ingestion effect of Bacillus subtilis natto*, 10 FOOD SCI. & TECH. RES. 17 (2004), incorporated by reference herein in its entirety. However, those two effects might partially be due to subtilisin NAT, although the mechanism for the enzyme to potentiate fibrinolysis in vivo is not yet fully understood. See, e.g., T. Urano, et al., *The profibrolytic enzyme subtilisin NAT purified from Bacillus subtilis claves and inactivates plasminogen activator inhibitor type 1*, 276 J. BIOLOGICAL CHEMISTRY 24690 (2001), incorporated by reference herein in its entirety.

"Thua nao" is a traditional fermented soybean food produced in northern Thailand. See, e.g., A. Leejeerajumnean, et al., *Volatile compounds in Bacillus-fermented soybean*, 81 J. SCI. FOOD & AGRICULTURE 525 (2001), incorporated by reference herein in its entirety. Typically, Thua nao is produced by first boiling and mashing soybeans, and then fermenting the soybeans in banana leaves for 2-3 days at ambient temperature. Alternatively, boiled, mashed soybeans are dried outdoors in the sun. Sun-dried Thua nao can be stored for several months at room temperature. See, e.g., P. Chantawannakul, et al., *Characterization of protease of Bacillus subtilis strain 38 isolated from traditionally fermented soybean in Northern Thailand*, 28 SCI. ASIA 241 (2002), incorporated by reference herein in its entirety. Similar sun-dried fermented soybean foods are also produced in Nepal, in Yunnan province of China, and in northern Laos and Myanmar. See, e.g., Y. Inatsu, et al., *Characterization of Bacillus subtilis strains isolated from fermented soybean foods in southeast Asia: comparison with B. subtilis (natto) starter strains*, 36 JAPAN AGRICULTURAL RES. QUARTERLY 525 (2001), incorporated by reference herein in its entirety. Thua nao and other naturally fermented soybean foods are thought to harbor *Bacillus subtilis* strains, which exhibit high potential for producing enzymes such as amylase and protease, and for producing health-promoting compounds such as PGA and protease NAT. Thua nao has been demonstrated to possess a diversity of *Bacillus subtilis*. See, e.g., Y. Inatsu, et al., *Characterization of Bacillus subtilis strains in Thua nao, a traditional fermented soybean food in northern Thailand*, 43 LETTERS IN APPLIED MICROBIOLOGY 237 (2006), incorporated by reference herein in its entirety.

Although the cultural history of *Bacillus subtilis* fermentation is well known, research on modern uses and consumption of *Bacillus subtilis* is comparatively very recent. Clinical trials have shown that *Bacillus subtilis* is safe for consumption, and beneficial for digestive health. *Bacillus subtilis* displays immunostimulating properties and antagonizes gastrointestinal pathogen infection by producing antimicrobial substances such as amicoumacins. See, e.g., Marie Lefevre, et al., *Probiotic strain Bacillus subtilis CU1 stimulates immune system of elderly during common infectious disease period: a randomized, double-blind placebo-controlled study*, 12 IMMUNITY & AGEING 24 (2015), incorporated by reference herein in its entirety.

The term "probiotic" means "for life" in Greek. It was first used in 1965 to name microorganisms that are beneficial to consume. The general health benefits of consuming probiotics have been shown in both animal and human studies. As a component of the human microbiome, *Bacillus subtilis* has the ability to promote gastrointestinal health, including helping its host in digestion, making it an ideal probiotic.

The term "probiotic," as used herein, can refer to viable microorganisms that promote or support a beneficial balance of the autochthonous microbial population of the gut. Alternatively, probiotics can refer to "live microorganisms that may confer a health benefit on the host." These bacterial strains are becoming extremely popular, not only in alternative circles, but also within the scientific community. Scientists have discovered that the microbes that live within animal intestines are important to their health. Animal and human species host at least 1000 different species of bacteria and fungi, and maintaining the right populations of each species is essential. Therefore, maintaining intestinal flora with probiotics is a logical step.

The notion of probiotics evolved from a theory first proposed by Elie Matchnikoff (Nobel laureate), who associated longevity with the consumption of fermented milk products. He postulated that the *Bacillus* present could positively modify the bacterial community structure of the colon, thus contributing to human health status. While not intending to be bound by any theory, the present disclosure is in general agreement with the current understanding of probiotics as used in foods and nutritional/dietary supplements for animals and humans.

The microbial population of the intestine is a highly dynamic and complex ecosystem having an estimated $10^{14}$ microorganisms representing more than 400 bacterial species. It has many functions in humans, including providing enzymes necessary for assimilation and/or synthesis of some nutrients, as well as in detoxifying certain harmful dietary compounds. In addition, the gastrointestinal flora provides a natural barrier against pathogens and can stimulate bowel motility and the immune system.

Probiotic formulations and blends should be able to recover and compete with established microflora in the colon to provide colonization and benefits for the host. For this purpose, they can use help from prebiotics such as inulin.

The gut microbiome influences myriad host functions, including nutrient acquisition, immune modulation, brain development, and behavior. Although human gut microbiota are recognized to change as we age, information regarding the structure and function of the gut microbiome during childhood is limited. A study using 16S rRNA gene and shotgun metagenomics sequencing characterized the structure, function, and variation of the healthy pediatric gut microbiome in a cohort of school-aged, pre-adolescent children (ages 7-12 years). The results showed a difference in the microbiome of the children vs. adults on many strains of bacteria. Children were enriched in *Bifidobacterium* spp., *Faecalibacterium* spp., and members of the Lachnospiraceae, while adults harbored greater abundances of *Bacteroides* spp. From a functional perspective, significant differences were detected with respect to the relative abundances of genes involved in vitamin synthesis, amino acid degradation, oxidative phosphorylation, and triggering mucosal inflammation. Children's gut communities were enriched in functions which may support ongoing development, while adult communities were enriched in functions associated with inflammation, obesity, and increased risk of adiposity. See, e.g., Hollister, et al., *Structure and function of the healthy pre-adolescent pediatric gut microbiome*, 3 MICROBIOME 36 (2015), incorporated by reference herein in its entirety.

Recently, probiotics therapy, evidenced by numerous randomized clinical trials ("RCTs") followed by meta analyses and Cochran reviews, has generated a great deal of renewed interest, due to its significant therapeutic effect on rotavirus-associated diarrhea in children in developed countries. The most commonly used strains of probiotics belong to the genera *Lactobacillus* and *Bifidobacterium*, *L. rhamnosus* GG, *Saccharomyces boulardii*, *Bacillus clausii*, mix of *L. delbrueckii* var *bulgaricus*, *Streptococcus thermophiles*, *L. acidophilus*, and *Bifidobacterium bifidum*, or *Enterococcus faecium* SF 68. The median duration of diarrhea was significantly shorter and the frequency was lower only in those children who received mixes of four bacterial strains. See, e.g., Dutta, et al., *Randomised controlled clinical trial of Lactobacillus sporogenes (Bacillus coagulans), used as a probiotic in clinical practice, on acute watery diarrhea in children*, 16 TROPICAL MED. INT'L HEALTH 555 (2011), incorporated by reference herein in its entirety.

Furthermore, the issue of the safe application of probiotics is not new or specific to older populations; however, there are aspects that are particular to this age group and that need to be addressed. As has been reviewed of late, the safety of application/consumption of a probiotic is linked to the potential vulnerability of the consumer to specific disease states. See, e.g., Rijkers, et al., *Guidance for substantiating the evidence for beneficial effects of probiotics: current status and recommendations for future research*, 140 J. NUTRITION 671S (2010), incorporated by reference herein in its entirety.

Older people are by definition more likely to present "at-risk" factors, which include immune compromise, central venous catheter, impaired intestinal barrier function, or consumption of broad-spectrum antibiotics to which the probiotic is resistant. See, e.g., Boyle, et al., *Probiotic use in clinical practice: what are the risks?*, 83 J. AM. CLINICAL NUTRITION 1256 (2006), incorporated by reference herein in its entirety. Probiotics have been consumed safely for a long time by the general population, exemplified by the incidence of only one case of *lactobacillus* septicemia among 10 million consumers in France over the course of a century. See, e.g., Bernardeau, et al., *Beneficial lactobacilli in food and feed: long-term use, biodiversity and proposals for specific and realistic safety assessments*, 30 FEMS MICROBIOLOGY REVS. 487 (2006), incorporated by reference herein in its entirety.

Nevertheless, the suitability of therapeutic application of probiotics in older subjects, as distinct from consumption of foods containing probiotic bacteria, should be considered individually and focus on specific needs. Compared with younger adults, populations of older adults consume a complex array of medications, ranging from antibiotics through to pharmaceutical compounds with potential but unknown effects upon the complex bacterial community in the intestine. For example, in the first 360 subjects enrolled in the ELDERMET project, 95 subjects had consumed antibiotics in the 4 weeks prior to their baseline microbiota determination, and 98% had consumed a recognized medicinal compound. See Rijkers, et al., 2010. Probiotics have recognized utility to mitigate the diarrheal side effects of antibiotics and to reduce the incidence of *Clostridum difficile*-associated colitis. See, e.g., Hickson, et al., *Use of probiotic Lactobacillus preparation to prevent diarrhea associated with antibiotics: randomized double blind placebo controlled trial*, 335 BMJ 80 (2007); C. M. Surawicz, et al., *Role of probiotics in antibiotic-associated diarrhea, Clostridium difficile-associated diarrhea, and recurrent Clostridium difficile-associated diarrhea*, 42 (Suppl. 2) J. CLINICAL GASTROENTEROLOGY S64 (2008); each of which is incorporated by reference herein in its entirety. Lifting the burden of infectious disease would be particularly beneficial in older populations.

Several recent comprehensive reviews have summarized the major benefits associated with probiotic consumption in older adults, and such benefits include increased levels of bifidobacteria, reduced constipation, enhanced innate immunity, and reduced inflammation. See, e.g., Pitkala, et al., *Fermented cereal with specific bifidobacteria normalizes bowel movements in elderly nursing home residents. A randomized, controlled trial*, 11 J. NUTRITION, HEALTH, & AGING 305 (2007); Gill, et al., *Enhancement of immunity in the elderly by dietary supplementation with the probiotic Bifidobacterium lactis HN019*, 74 AM. J. CLINICAL NUTRITION 833 (2001); Ouwehand, et al., *Bifidobacterium microbiota and parameters of immune function in elderly subjects*, 53 FEMS IMMUNOLOGY & MEDICAL MICROBIOLOGY 18 (2008); each of which is incorporated by reference herein in its entirety. Administration of yoghurt fermented by *L. bulgaricus* to older people (n=142; a median age of 74.5 years) significantly reduced the incidence and severity of winter colds and general upper respiratory symptoms. This improvement was accompanied by an increase in natural killer cell activity in the subjects receiving the yoghurt. See, e.g., Makino, et al., *Reducing the risk of infection in the elderly by dietary intake of yoghurt fermented with Lactobacillus delbrueckii ssp. Bulgaricus OLL1073R-1*, 104 BR. J. NUTRITION 998 (2010), incorporated by reference herein in its entirety.

Preclinical validation of beneficial effects in in vitro systems or animal models may thus be beneficial for strain selection, but obviously cannot replace human trials. Older adults as a group in society will typically span a greater range in health status (from healthy and independent to frail and dependent upon assistance). Older adults are known to have microbiota in flux that varies significantly more between individuals than in a younger adult population. These factors should be borne in mind when designing clinical trials.

Recent analyses of the microbiota of older adults in Ireland confirmed that the prevalence of the genus *Faecalibacterium* varied significantly between individuals, supporting the notion that levels of this organism might be suitable for therapeutic intervention in older people with intestinal inflammation. Administration of prebiotics, or by administering probiotics that target competing elements in the microbiota, is conceptual at this time. See, e.g., S. Cusack, et al., *How Beneficial is the Use of Probiotic Supplements for the Aging Gut?*, 7 AGING HEALTH 179 (2011), incorporated by reference herein in its entirety.

Furthermore, domesticated animals and/or pet animals can benefit from probiotics. Pet animals may include small or large domestic mammals, for example, but are not limited to, dogs, cats, horses, sheep, cows, cattle, other bovine species, pigs, goats, rabbits, and the like. Also contemplated are small rodent species, including rats, mice, hamsters, gerbils, guinea pigs, and the like.

All dogs can benefit from probiotics, which aid digestion and modulate the immune system. Probiotics produce short-chain fatty acids ("SCFAs"), which inhibit the growth and activity of harmful bacteria, such as *E. coli, Salmonella*, and *Clostridium perfringens*, as well as provide other benefits to the intestines. Human studies have documented the effectiveness of certain strains in treating diarrhea, irritable bowel syndrome, and intestinal inflammation. Probiotics used in dogs may help prevent urinary tract infections, and can even reduce allergic reactions by decreasing intestinal permeability and controlling inflammation.

Research looking at the effectiveness of probiotics in dogs is not nearly as extensive as research of the effectiveness in humans. Still, there are studies that suggest that probiotics can improve or maintain the health of dogs. The diseases that have been investigated so far to determine the effectiveness of probiotics in dogs are acute diarrhea and contact dermatitis (skin allergy).

Acute diarrhea in dogs is diarrhea that starts suddenly and usually results on its own. Probiotics have been tested on several types of acute diarrhea, specifically diarrhea caused by dietary sensitivity and diarrhea caused by the ingestion of an intestinal pathogen. In dogs with dietary sensitivity, treatment with *Lactobacillus acidophilus* in combination with the diarrhea-provoking food led to some improvement in bowel movements. Better results, however, were observed when probiotics were applied as treatments for acute diarrhea caused by a stomach virus.

Probiotic species known to benefit dogs include *Bacillus coagulans*. *Bifidobacterium animalis* has been shown to reduce the time for acute diarrhea to resolve in dogs. *Lactobacillus acidophilus* improved frequency and quality of stools in sensitive dogs. *Lactobacillus rhamnosus* strain GG ("LGG") is effective in preventing and treating diarrhea in humans, and may benefit dogs as well.

*Bifidobacterium animalis* has been studied more in detail. *Bifidobacterium animalis* was chosen for further research because initial studies showed that *Bifidobacterium animalis* had an above-average ability to bind to the gut, a characteristic often associated with beneficial bacteria. Initial studies in dogs showed that *Bifidobacterium animalis* could reduce the pathogenicity of *Salmonella typhiurium* and Clostridia *difficile*, which are bacteria known to induce acute diarrhea. And later, during a treatment study, it was found that *Bifidobacterium animalis* could help acute diarrhea resolve faster.

Dermatitis usually caused by a skin allergy. To treat the dermatitis, one needs to address the underlying immune problems. During allergic responses, the immune system considers a normally harmless substance as a threat. In dogs with a skin allergy, contact of the allergen on the skin causes an immune reaction leading to the classic symptoms of inflammation: itching, redness, and heat. Unfortunately, dogs that develop allergies are usually genetically predisposed to the condition. This means that prevention has to happen at a young age or even when a puppy is still in the womb.

Scientists looked at the ability of *L. rhamnosus* to change the course of allergy in dogs with a genetic predisposition towards allergy. *L. rhamnosus* was given during pregnancy to the mother and to the puppies during weaning. Unfortunately, while there were some significant changes in immunological parameters, the puppies had no real improvements, but a follow-up study performed three years later in the grownup puppies showed that there were differences in the long-term. The immune system was geared towards anti-inflammatory reactions, and the dogs had less dermatitis.

Additionally, many products on the market are of dubious quality. A study testing 19 commercial pet foods, all claiming to contain probiotics, determined that none of the feeds contained what was written on the packages. Only 53% of the tested commercial pet foods contained at least one of the probiotics species listed, and 26% of the tested commercial pet foods had no live bacteria. These results would suggested that using pet food fortified with probiotics is not the wisest route for providing one's pet dog with beneficial bacteria. The recommendation would be to seek out a quality probiotic with the help of a veterinarian.

Probiotics are measured by colony forming units ("CFUs"). Few studies have been done to determine effective dosages, but effective dosages are usually in the hundreds of millions of CFUs or higher. If probiotics are being used to help with digestion, probiotics should be taken with meals, but otherwise the probiotics may survive better if taken between meals, particularly if taken with liquids that help to dilute stomach acid and move the probiotics more quickly into the digestive tract (for example, given after the dog takes a big drink). Probiotics may be given short-term or long-term.

Several studies have revealed that some probiotics products in the market have deficiencies in the viabilities of probiotic strain(s), especially in products containing Bifido-bacteria. These deficiencies in viability may be due to storage, manufacturing, or food technology setbacks, such as inappropriate packing materials that could affect probiotic stability through variations in oxygen permeability. In the past two decades, there has been renewed interest in the study of the nutritional and therapeutic aspects of the mentioned products. It is widely accepted that probiotics may exert positive influence on the host through modulation of the endogenous ecosystem and stimulation of the immune system, as well as maintenance of healthy intestinal microflora. However, research suggests that health benefits can be strain-specific and vary by amount ingested and duration administered, even in pets.

One useful *Bacillus subtilis*-containing composition is DE111®, available from Deerland Enzymes, Inc. (Kennesaw, Georgia, United States). DE111® is an isolated strain of *Bacillus subtilis* subspecies *inaquosorum* having accession number NRRL B-67989. The *Bacillus subtilis* subspecies *inaquosorum* (DE111®) strain was deposited with the Agricultural Research Service Culture Collection (NRRL), an International Depositary Authority, 1815 N. University Street, Peoria, Illinois, 61604, United States, under the Budapest Treaty on the International Recognition of the Deposit of Microorganisms, on Sep. 28, 2020 and was accepted and found to be viable on Sep. 28, 2020, and assigned accession number NRRL B-67989. The DE111® strain is a biologically pure culture prepared by a proprietary process.

The *Bacillus subtilis* DE111® (*Bacillus subtilis* subspecies *inaquosorum* having Accession No. NRRL B-67989) strain has certain properties, which, surprisingly, have been found to make the strain well-suited for use as a probiotic. Spores of *Bacillus subtilis* are viable under a wide temperature and pH range. Without being bound by any particular theory, it is thought that the ability of *Bacillus subtilis* DE111® to form spores that protect the microbes from harsh conditions until they enter an environment ripe for germination, such as the GI tract, makes *Bacillus* particularly well-suited for use as a probiotic.

In one aspect of the invention, compositions administered to patients in need thereof according to the methods of the present disclosure comprise mutants of *Bacillus subtilis* DE111® (*Bacillus subtilis* subspecies *inaquosorum* having Accession No. NRRL B-67989) having all the identifying characteristics of *Bacillus subtilis* DE111®. Such mutants may have DNA sequence identity to *Bacillus subtilis* DE111® of at least about 90%, at least about 91%, at least about 92%, at least about 93%, at least about 94%, at least about 95%, at least about 96%, at least about 97%, at least about 98%, or at least about 99%. In some embodiments, mutants are spontaneous mutants. The teen spontaneous mutant refers to mutants that arise from *Bacillus subtilis* DE111® without the intentional use of mutagens. Such spontaneous mutants may be obtained by classical methods, such as growing the *Bacillus subtilis* DE111® strain in the presence of a certain antibiotic to which the parent is susceptible, and testing any resistant mutants for improved biological activity or, in this application, improved ability to reduce the symptoms of gastrointestinal irregularity. Other methods for identifying spontaneous mutants will be known to those of ordinary skill in the art.

All references in this application to *Bacillus subtilis* DE111® (*Bacillus subtilis* subspecies *inaquosorum* having Accession No. NRRL B-67989) or its mutants refer to bacteria that have been isolated from nature and are grown by humans, for example, in the laboratory or under industrial conditions.

*Bacillus subtilis* DE111® (*Bacillus subtilis* subspecies *inaquosorum* having Accession No. NRRL B-67989) cells may be present in the compositions administered to patients in need thereof according to the methods of the present disclosure as spores (which are dormant), as vegetative cells (which are growing), as transition state cells (which are transitioning from growth phase to sporulation phase) or as a combination of all of these types of cells. In some embodiments, the composition comprises mainly spores. In other embodiments, the composition comprises spores and metabolites produced by the cells during fermentation before they sporulate, as described below.

Compositions administered to patients in need thereof according to the methods of the present disclosure can be obtained by culturing *Bacillus subtilis* DE111® (*Bacillus subtilis* subspecies *inaquosorum* having Accession No. NRRL B-67989) or its mutants according to methods well known in the art. Conventional large-scale microbial culture processes include submerged fermentation, solid state fermentation, or liquid surface culture. Towards the end of fermentation, as nutrients are depleted, *Bacillus subtilis* DE111® cells begin the transition from growth phase to sporulation phase, such that the final product of fermentation is largely spores, metabolites, and residual fermentation medium. Sporulation is part of the natural life cycle of *Bacillus subtilis* DE111® and is generally initiated by the cell in response to nutrient limitation. Fermentation is configured to obtain high levels of colony forming units of *Bacillus subtilis* DE111® and to promote sporulation. The bacterial cells, spores, and metabolites in culture media resulting from fermentation may be used directly or concentrated by conventional industrial methods, such as centrifugation, tangential-flow filtration, depth filtration, and evaporation. In some embodiments, the concentrated fermentation broth is washed, for example, via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation. The resulting dry products may be further processed, such as by milling or granulation, to achieve a specific particle size or physical format. Carriers, described below, may also be added post-drying.

In embodiments in which compositions formulated separately from food or drink are administered to patients in need thereof according to the methods of the present disclosure, the concentration on a weight by weight basis (w/w) of (i) *Bacillus subtilis* DE111® (*Bacillus subtilis* subspecies *inaquosorum* having Accession No. NRRL B-67989) or its mutants, (ii) metabolites of *Bacillus subtilis* DE111® or its mutants, or (iii) combinations of cells and metabolites in the formulated composition may be about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, or about 95%. In some embodiments of compositions administered to patients in need thereof according to the methods of the present disclosure, where the concentrated formulation broth has been washed and dried without heat, such as via freeze drying, the concentration of *Bacillus subtilis* DE111® or its mutants in the final composition may be from about 90% to about 100%.

In certain embodiments, compositions administered to individuals in need thereof according to methods of the present disclosure are administered to treat gastrointestinal irregularity. An effective amount of a composition administered to an individual in need thereof according to the methods of the present disclosure is an amount effective to reduce gastrointestinal irregularity in comparison to an individual who has not been administered the composition but otherwise has been administered the same diet as has an individual administered the composition according to methods of the present disclosure and has the same symptoms as an individual administered the composition. In other embodiments, an effective amount is an amount need to prevent recurrence or to reduce symptoms of gastrointestinal irregularity.

In certain embodiments, gastrointestinal irregularity is characterized by symptoms including, but not limited to, occasional constipation and/or diarrhea, which can be burdensome gastrointestinal issues occurring in many individuals. Treatment of constipation and/or diarrhea remains challenging. Health professionals use the Bristol Stool Scale to classify stool type, as it may be difficult to differentiate between normal and abnormal stools. The Bristol Stool Scale can help assess the consistence and the time stools spent in the bowels. Type 1 stools have spent the longest time, while type 7 stools spend the least time. FIG. 1 depicts the Bristol Stool Chart ("BSC").

The Bristol Stool Scale is a diagnostic medical tool, which is designed to classify the form of human feces into seven categories, and which is used in both clinical and experimental fields. See, e.g., H. Koh, et al., *Simple diagnostic approach to childhood fecal retention using the Leech score and Bristol stool form scale in medical practice*, 25 J. GASTROENTEROLOGY & HEPATOLOGY 334 (2010); M. Corsetti, et al., *Rectal distensibility and symptoms after stapled and Milligan-Morgan operation for hemorrhoids*, 13 J. GASTROINTESTINAL SURGERY 2245 (2009); H. J. Wang, et al., *A Randomised, Controlled Comparison of Low-Dose Polyethylene Glycol 3350 plus Electrolytes with Ispaghula Husk in the Treatment of Adults with Chronic Functional Constipation*, 24 CLINICAL DRUG INVESTIGATION 569 (2004); each of which is incorporated by reference herein in its entirety. The Bristol Stool Scale is sometimes also referred to as the Bristol Stool Chart ("BSC"), Bristol stool form scale, or BSF scale. See, e.g., G. Amarenco, *Bristol Stool Chart: étude prospective et monocentrique de "l'introspection fécale" chez des sujets volontaires [Bristol Stool Chart: Prospective and monocentric study of "stools introspection" in healthy subjects]*, 24 PROGRÈS EN UROLOGIE 708 (2014), incorporated by reference herein in its entirety. The Bristol Stool Scale was developed at the Bristol Royal Infirmary as a clinical assessment tool in 1997, and is widely used as a research tool to evaluate the effectiveness of treatments for various diseases of the bowel, as well as a clinical communication aid, including being part of the diagnostic triad for irritable bowel syndrome. See, e.g., BETTY J. ACKLEY & GAIL B. LADWIG, NURSING DIAGNOSIS HANDBOOK: AN EVIDENCE-BASED GUIDE TO PLANNING CARE (10th ed., Mosby Elsevier 2013); G. Riegler & I. Esposito, *Bristol scale stool form. A still valid help in medical practice and clinical research*, 5 TECHNIQUES IN COLOPROCTOLOGY 163 (2001); NATIONAL COLLABORATING CENTRE FOR NURSING AND SUPPORTIVE CARE (UNITED KINGDOM), *Irritable Bowel Syndrome in Adults: Diagnosis and Management of Irritable Bowel Syndrome in Primary Care, NICE Clinical Guidelines* (2008); each of which is incorporated by reference herein its entirety. According to the Bristol Stool Scale, the seven types of stool are: Type 1—Separate hard lumps, like nuts (hard to pass) (also known as goat faeces); Type 2—Sausage-shaped, but lumpy; Type 3—Like a sausage but with cracks on its surface; Type 4—Like a sausage or snake, smooth and soft; Type 5—Soft blobs with clear cut edges (easy to pass); Type 6—Fluffy pieces with ragged edges, a mushy stool; Type 7—Watery, no solid pieces, entirely liquid. See, e.g., M. Minguez Pérez & A. Benages Martinez, *The Bristol scale—a useful system to assess stool form?*, 101 REVISTA ESPANOLA DE ENFERMEDADES DIGESTIVAS 305 (2009), incorporated by reference herein in its entirety.

The Bristol Stool Scale has been validated in Spanish, Brazilian Portugese, and Polish versions. See, e.g., D. Parés, et al., *Adaptation and validation of the Bristol scale stool form translated into the Spanish language among health professionals and patients*, 101 REVISTA ESPANOLA DE ENFERMEDADES DIGESTIVAS 312 (2009); Y. Maestre, et al., *Prevalence of fecal incontinence and its relationship with bowel habit in patients attended in primary care*, 135 MEDICINA CLINICA 59 (2010); A. P. Martinez & G. R. de Azevedo, *The Bristol Stool Form Scale: its translation to Portugese, cultural adaptation and validation*, 20 REVISTA LATINO-AMERICANA DE ENFERMAGEM 583 (2012); K. Wojtyniak, et al., *Translation to Polish, cross-cultural adaptation, and validation of the Bristol Stool Form Scale among healthcare professionals and patients*, 13 PRZEGLAD GASTROENTEROLOGICZNY 35 (2018); each of which is incorporated by reference herein in its entirety. A version of the Bristol Stool Scale has been designed and validated for pediatrics. See, e.g., B. P. Chumpitazi, et al., *Creation and initial evaluation of a stool form scale for children*, 157 J. PEDIATRICS 594 (2010); D. Candy & S. Paul, *Go with the flow: in childhood constipation*, 21 J. FAMILY HEALTH CARE 35 (2011); each of which is incorporated by reference herein in its entirety. Research conducted on irritable bowel syndrome in the 2000s, fecal incontinence, and the gastrointestinal complications of HIV, have used the Bristol Stool Scale as an easy-to-use diagnostic tool. See, e.g., S. Yilmaz, et al., *The epidemiological aspects of irritable bowel syndrome in Southeastern Anatolia: a stratified randomized community-based study*, 59 INT'L J. CLINICAL PRACTICE 361 (2005); P. Adibi, et al., *Bowel habit reference values and abnormalities in young Iranian healthy adults*, 52 DIGESTIVE DISEASES & SCIS. 1810 (2007); A. K. Macmillan, et al., *Design and validation of a comprehensive fecal incontinence questionnaire*, 51 DISEASES OF THE COLON & RECTUM 1502 (2008); J. M. Chung, et al., *An epidemiologic study of voiding and bowel habits in Korean children: a nationwide multicenter study*, 76 UROLOGY 215 (2010); G. El-Gazzaz, et al., *Sacral neuromodulation for the treatment of fecal incontinence and urinary incontinence in female patients: long-term follow-up*, 24 INT'L J. COLORECTAL DISEASE 1377 (2009); J. Tinmouth, et al., *Evaluation of Stool frequency and stool form as measures of HIV-related diarrhea*, 8 HIV CLINICAL TRIALS 421 (2007); M. Zutshi, et al., *Ten-year outcome after anal sphincter repair for fecal incontinence*, 52 DISEASES OF THE COLON & RECTUM 1089 (2009); each of which is incorporated by reference herein in its entirety.

Since 2010, several clinical studies have used the Bristol Stool Scale as a diagnostic tool validated for recognition and evaluation of response to various treatments, such as probiotics, moxicombustion, laxatives in the elderly, preparing Ayurvedic polyphytotherapy filed TLPL/AY, psyllium, mesalazine, methylnaltrexone, and oxycodone/naloxone, or for assessment of the response to physical activity in athletes. See, e.g., T. Sakai, et al., *Fermented milk containing Lactobacillus casei strain Shirota reduces incidence of hard or lumpy stools in healthy population*, 62 INT'L J. OF FOOD SCIS. & NUTRITION 423 (2011); G. Riezzo, et al., *Randomised clinical trial: efficacy of Lactobacillus paracasei-enriched artichokes in the treatment of patients with functional constipation—a double-blind, controlled, crossover study*, 35 ALIMENTARY PHARMACOLOGY & THERAPEUTICS 441 (2012); J. E. Park, et al., *The effectiveness of moxibustion for the treatment of functional constipation: a randomized, sham-controlled, patient blinded, pilot clinical trial*, 11 BMC COMPLEMENTARY & ALTERNATIVE MEDICINE 124 (2011); G. S. Fosnes, et al., *Effectiveness of laxatives in elderly—a cross sectional study in nursing homes*, 11 BMC GERIATRICS 76 (2011); R. Munshi, et al., *An open-label, prospective clinical study to evaluate the efficacy and safety of TLPL/AY/01/2008 in the management of functional constipation*, 2 J. AYURVEDA & INTEGRATIVE MEDICINE 144 (2011); F. Pucciani, et al., *Usefulness of psyllium in rehabilitation of obstructed defecation*, 15 TECHNIQUES IN COLOPROCTOLOGY 377 (2011); M. Bafutto, et al., *Treatment of postinfectious irritable bowel syndrome* and *noninfective irritable bowel syndrome with mesalazine*, 48 ARQUIVOS DE GASTROENIEROLOGIA 36 (2011); E. Michna, et al., *Subcutaneous methylnaltrexone for treatment of opioid-induced constipation in patients with chronic, nonmalignant pain: a randomized controlled study*, 12 J. PAIN 554 (2011); K. E. Clemens, et al., *Bowel function during pain therapy with oxycodone/naloxone prolonged-release tablets in patients with advanced cancer*, 65 INT'L J. CLINICAL PRACTICE 472 (2011); H. Strid, et al., *Effect of heavy exercise on gastrointestinal transit in endurance athletics*, 46 SCANDINAVIAN J. GASTROENTEROLOGY 673 (2011); each of which is incorporated by reference herein in its entirety.

Patients with stools classified as type 1 or type 2 according to FIG. 1 are individuals who suffer from constipation. Without being bound by theory, the gastrointestinal irregularity associated with constipation can be the result of many factors including a poor diet, excess stress, the normal aging process, or acute dysbiosis resulting from antibiotic treatment or low fiber diets. When there is a balance in the normal flora of the gut, beneficial bacteria can hold water facilitating the passing of feces. When absent, the stools lack a normal amorphous quality and become formed lumps that can be hard and abrasive. The typical diameter of these lumps can range from 1 to 2 cm, and can be painful to pass due to their hard and scratchy nature. On the other hand, patients with stool that falls within the 5-7 range according to FIG. 1 may have a hyperactive colon (e.g., fast motility) or excess dietary potassium. Such patients may suffer from sudden dehydration or stress-related spikes in blood pressure; both conditions can cause the rapid release of water and potassium from blood plasma into the intestinal cavity. In addition, stools in this range are indicative of a hypersensitive personality prone to stress, diets rich in spices, fats, high mineral contents, and the use of osmotic (e.g., mineral salts) laxatives.

In certain embodiments of the methods of the present disclosure, compositions are administered to patients in need thereof to treat gastrointestinal irregularity by reducing the symptoms of such disorder or reducing the rate of occurrence or recurrence of such disorder. In other embodiments of the methods of the present disclosure, compositions are administered to patients in need thereof to maintain or promote gastrointestinal regularity.

Thus, in line with the above, embodiments of the present disclosure are directed to methods of treating gastrointestinal irregularity, maintaining gastrointestinal regularity, promoting gastrointestinal regularity, restoring gastrointestinal regularity, and maintaining healthy gut microflora by administering to a patient in need thereof a composition comprising *Bacillus subtilis* DE111® (*Bacillus subtilis* subspecies *inaquosorum* having Accession No. NRRL B-67989), a mutant of *Bacillus subtilis* DE111®, metabolites of *Bacillus subtilis* DE111® or its mutants, or combinations of *Bacillus subtilis* DE111® or a mutant and metabolites of *Bacillus subtilis* DE111® or its mutants.

Maintenance of healthy gut microflora refers to decreasing (by killing or inhibiting the growth of) harmful, disease-causing microorganisms of public health concern and/or increasing or maintaining healthy levels of beneficial bacteria, such as Lactobacilli and Bifidobacteria, as compared to a human to which the methods of the present disclosure have not been applied. Without wishing to be bound by any particular theory, it is thought that increases to beneficial bacteria may be caused by stimulating growth of such bacteria or simply by selectively decreasing pathogenic bacteria, thereby giving the beneficial bacteria more space to grow and to attach to the gut wall and/or more efficient access to nutrients and growth factors. In addition, or alternatively, beneficial bacteria may modify the virulence factors of pathogenic bacteria, thus decreasing the virulence of the pathogenic bacteria. Harmful, disease-causing bacteria that may be decreased by the methods of the present disclosure include *Clostridia* spp. (such as *perfringens* and *dificille*), *Listeria* spp. (such as *Moncytogenes, seeligeri*, and *welshimeri*), *Salmonella* spp. (such as *enterica, arizonae, typhirium, enteridis*, and *bonglori*), *E. coli, Enterococus* spp. (such as *faecalis* and *faecium*), *Campylobacter, Aeromonas* spp., *Staphylococcus aureus, Shigella dysenteria*, and *Vibrio* spp. In some embodiments, harmful, disease-causing microorganisms may be reduced by about 0.5 log, about 1 log, about 2 log, about 3 log, about 4 log, or about 5 log.

In other embodiments, the methods of the present invention may also be used to promote or restore gastrointestinal regularity after administration of therapeutic amounts of antibiotics by inhibiting growth of pathogenic bacteria and/or increasing or maintaining growth of beneficial bacteria. The term "therapeutic amount" refers to an amount sufficient to ameliorate or reverse a disease state in a human.

In another aspect, compositions administered according to methods of the present disclosure comprising *Bacillus subtilis* DE111® (*Bacillus subtilis* subspecies *inaquosorum* having Accession No. NRRL B-67989), its mutants, and/or metabolites of *Bacillus subtilis* DE111® and/or its mutants may further include or be administered with other probiotics, such as other bacterial spore formers. Examples of probiotics are provided in H. A. Hong, et al., The use of bacterial spore formers as probiotics, 29 FEMS MICROBIOLOGY REVS. 813 (2005), incorporated by reference herein in its entirety.

In yet another aspect, compositions administered according to methods of the present disclosure may include or be administered with (either at the same time or at different times) anti-diarrheal agents, anti-gas agents, dietary fibers, antibiotics, such as methotrexate, anti-inflammatory drugs, amino acids, electrolytes, vitamins, and minerals.

In embodiments in which the compositions administered according to methods of the present disclosure comprise *Bacillus subtilis* DE111® (*Bacillus subtilis* subspecies *inaquosorum* having Accession No. NRRL B-67989) or its mutants, the bacteria should be administered in an amount that is effective to treat gastrointestinal irregularity, maintain gastrointestinal regularity, promote gastrointestinal regularity, restore gastrointestinal regularity, and/or maintain healthy gut microflora. In embodiments in which the compositions are being administered to treat gastrointestinal irregularity, maintain gastrointestinal regularity, promote gastrointestinal regularity, restore gastrointestinal regularity, and/or maintain healthy gut microflora, the compositions should be administered at effective total daily doses of from about $1 \cdot 10^3$ CFU *Bacillus subtilis* DE111® to about $1 \cdot 10^{15}$ CFU *Bacillus subtilis* DE111®. In other embodiments in which the compositions are being administered to treat gastrointestinal irregularity, maintain gastrointestinal regularity, promote gastrointestinal regularity, restore gastrointestinal regularity, and/or maintain healthy gut microflora, the compositions should be administered at effective total daily doses of from about $1 \cdot 10^4$ CFU *Bacillus subtilis* DE111® to about $1 \cdot 10^{14}$ CFU *Bacillus subtilis* DE111®. In yet other embodiments in which the compositions are being administered to treat gastrointestinal irregularity, maintain gastrointestinal regularity, promote gastrointestinal regularity, restore gastrointestinal regularity, and/or maintain healthy gut microflora, the compositions should be administered at effective total daily doses of from about $1 \cdot 10^5$ CFU Bacillus subtilis DE111® to about $1·10^{13}$ CFU Bacillus subtilis DE111®. In yet other embodiments in which the compositions are being administered to treat gastrointestinal irregularity, maintain gastrointestinal regularity, promote gastrointestinal regularity, restore gastrointestinal regularity, and/or maintain healthy gut microflora, the compositions should be administered at effective total daily doses of from about $1·10^6$ CFU Bacillus subtilis DE111® to about $1·10^{12}$ CFU Bacillus subtilis DE111®. In yet other embodiments in which the compositions are being administered to treat gastrointestinal irregularity, maintain gastrointestinal regularity, promote gastrointestinal regularity, restore gastrointestinal regularity, and/or maintain healthy gut microflora, the compositions should be administered at effective total daily doses of from about $1·10^8$ CFU Bacillus subtilis DE111® to about $1·10^{11}$ CFU Bacillus subtilis DE111®. In yet other embodiments, a preferred effective total daily dose range is from about $1·10^9$ CFU Bacillus subtilis DE111® to about $1·10^{10}$ CFU Bacillus subtilis DE111®. In yet another embodiment, Bacillus subtilis DE111® can be provided in a daily dose of about $1·10^9$ CFU for about 1, 2, or 3 months, up to a total of about 105 days.

In an embodiment, administration of a Bacillus subtilis DE111® (Bacillus subtilis subspecies inaquosorum having Accession No. NRRL B-67989) dose at about 1 billion CFU per day statistically improved occasional constipation and diarrhea while helping to maintain gastrointestinal health. In contrast, the testing group administered placebo composition did not generate similar improvements.

In certain embodiments, the compositions administered according to the methods of the present disclosure may also include one or more excipients, most preferably one or more nutraceutical or pharmaceutical excipients. Compositions containing one or more excipients and incorporating one or more probiotics can be prepared by procedures known in the art. Optionally, compositions can include one or more adjuvants, excipients, carriers, buffers, diluents, and/or other customary pharmaceutical auxiliaries. For example, probiotics can be formulated into tablets, capsules, powders, suspensions, solutions for oral administration, solutions for parenteral administration including intravenous, intradermal, intramuscular, and subcutaneous administration, and solutions for application onto patches for transdermal application with common and conventional carriers, binders, diluents, and excipients.

In certain embodiments, nutraceutical compositions administered according to the methods of the present disclosure may be administered in combination with a pharmaceutically acceptable carrier. In certain embodiments, the active ingredients in such formulations may comprise from about 1% by weight to about 99% by weight. In other embodiments, the active ingredients in such formulations may comprise from about 0.1% by weight to about 99.9% by weight. "Pharmaceutically acceptable carrier" means any carrier, diluent, or excipient that is compatible with the other ingredients of the formulation and not deleterious to the user. Useful excipients include, but are not limited to, microcrystalline cellulose, magnesium stearate, calcium stearate, any acceptable sugar (e.g., mannitol, xylitol), and the like, and for cosmetic use, an oil-base is preferred.

Methods of Treating Gastrointestinal Irregularity, Maintaining Gastrointestinal Regularity, Promoting Gastrointestinal Regularity, Restoring Gastrointestinal Regularity, and/or Maintaining Healthy Gut Microflora In an embodiment, a method of treating gastrointestinal irregularity in an individual can include the steps of:
(a) administering orally to the individual a composition comprising Bacillus subtilis in a dose of from about $1·10^8$ CFU per day to about $1·10^{11}$ CFU per day for at least 15 days;
wherein the gastrointestinal irregularity of the individual decreases.

The method described herein effects a treatment of gastrointestinal irregularity in an individual.

In another embodiment, a method of treating gastrointestinal irregularity in an individual can include the steps of:
(a) administering orally to the individual a composition comprising Bacillus subtilis in a dose of about $1·10^9$ CFU per day for at least 15 days;
wherein the gastrointestinal irregularity of the individual decreases.

The method described herein effects a treatment of gastrointestinal irregularity in an individual.

In yet another embodiment, a method of treating gastrointestinal irregularity in an individual can include the steps of:
(a) administering orally to the individual a composition comprising Bacillus subtilis in a dose of about $1·10^9$ CFU per day for at least 30 days;
wherein the gastrointestinal irregularity of the individual decreases.

The method described herein effects a treatment of gastrointestinal irregularity in an individual.

In yet another embodiment, a method of treating gastrointestinal irregularity in an individual can include the steps of:
(a) administering orally to the individual a composition comprising Bacillus subtilis in a dose of about $1·10^9$ CFU per day for at least 60 days;
wherein the gastrointestinal irregularity of the individual decreases.

The method described herein effects a treatment of gastrointestinal irregularity in an individual.

In yet another embodiment, a method of treating gastrointestinal irregularity in an individual can include the steps of:
(a) administering orally to the individual a composition comprising Bacillus subtilis in a dose of about $1·10^9$ CFU per day for at least 90 days;
wherein the gastrointestinal irregularity of the individual decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:
(a) administering orally to the individual a composition comprising Bacillus subtilis in a dose of from about $1·10^8$ CFU per day to about $1·10^{11}$ CFU per day for at least 15 days;
wherein the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 15 days;

wherein the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 30 days;

wherein the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 60 days;

wherein the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 90 days;

wherein the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of from about 1·10$^8$ CFU per day to about 1·10$^{11}$ CFU per day for at least 15 days; and (b) measuring the individual's bowel movements according to the Bristol Stool Scale;

wherein steps (a) and (b) are repeated at least until the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 15 days; and (b) measuring the individual's bowel movements according to the Bristol Stool Scale;

wherein steps (a) and (b) are repeated at least until the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 30 days; and (b) measuring the individual's bowel movements according to the Bristol Stool Scale;

wherein steps (a) and (b) are repeated at least until the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 60 days; and (b) measuring the individual's bowel movements according to the Bristol Stool Scale;

wherein steps (a) and (b) are repeated at least until the frequency of the individual's 24-hour episodes per month of bowel movements measuring 1 or 2 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of about 1·10$^9$ CFU per day for at least 90 days; and (b) measuring the individual's bowel movements according to the Bristol Stool Scale;

wherein steps (a) and (b) are repeated at least until the frequency of the individual's 24-hour episodes per month of bowel movements measuring 1 or 2 on the Bristol Stool Scale decreases.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of from about $1 \cdot 10^8$ CFU per day to about $1 \cdot 10^{11}$ CFU per day for at least 15 days;

wherein the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for at least 15 days;

wherein the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for at least 30 days;

wherein the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for at least 60 days;

wherein the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for at least 90 days;

wherein the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of from about $1 \cdot 10^8$ CFU per day to about $1 \cdot 10^{11}$ CFU per day for at least 15 days; and (b) measuring the individual's bowel movements according to the Bristol Stool Scale;

wherein steps (a) and (b) are repeated at least until the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for at least 15 days; and (b) measuring the individual's bowel movements according to the Bristol Stool Scale;

wherein steps (a) and (b) are repeated at least until the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for at least 30 days; and (b) measuring the individual's bowel movements according to the Bristol Stool Scale;

wherein steps (a) and (b) are repeated at least until the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for about 60 days; and (b) measuring the individual's bowel movements according to the Bristol Stool Scale;

wherein steps (a) and (b) are repeated at least until the frequency of the individual's 24-hour episodes per month of bowel movements measuring 6 or 7 on the Bristol Stool Scale decreases.

The method described herein effects a treatment of gastrointestinal irregularity in an individual.

In yet another embodiment, a method of treating gastrointestinal irregularity in an individual, wherein the individual has at least one 24-hour episode per month of bowel movements measuring 6 or 7 on the Bristol Stool Scale, can include the steps of:

(a) administering orally to the individual a composition comprising *Bacillus subtilis* in a dose of about $1 \cdot 10^9$ CFU per day for about 90 days; and (b) measuring the individual's bowel movements according to the Bristol Stool Scale;

wherein steps (a) and (b) are repeated at least until the frequency of the individual's 24-hour episodes per month of bowel movements measuring 6 or 7 on the Bristol Stool Scale decreases.

The method described herein effects a treatment of gastrointestinal irregularity in an individual.

In an embodiment, a method of maintaining gastrointestinal regularity in an individual can include the steps of:

(a) administering orally to the individual a composition comprising *Bacillus subtilis* in a dose of from about $1 \cdot 10^8$ CFU per day to about $1 \cdot 10^{11}$ CFU per day for at least 15 days;

wherein the frequency of the individual's 24-hour episodes per month of bowel movements measuring 1 or 2 on the Bristol Stool Scale does not increase during the at least 15 days of administration.

The method described herein effects maintenance of gastrointestinal regularity in an individual.

In another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 15 days;

wherein the frequency of the individual's 24-hour episodes per month of bowel movements measuring 1 or 2 on the Bristol Stool Scale does not increase during the at least 15 days of administration.

The method described herein effects maintenance of gastrointestinal regularity in an individual.

In yet another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 30 days;

wherein the frequency of the individual's 24-hour episodes per month of bowel movements measuring 1 or 2 on the Bristol Stool Scale does not increase during the at least 30 days of administration.

The method described herein effects maintenance of gastrointestinal regularity in an individual.

In yet another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 60 days;

wherein the frequency of the individual's 24-hour episodes per month of bowel movements measuring 1 or 2 on the Bristol Stool Scale does not increase during the at least 60 days of administration.

The method described herein effects maintenance of gastrointestinal regularity in an individual.

In yet another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 90 days;

wherein the frequency of the individual's 24-hour episodes per month of bowel movements measuring 1 or 2 on the Bristol Stool Scale does not increase during the at least 90 days of administration.

In yet another embodiment, a method of maintaining gastrointestinal regularity in an individual can include the steps of:

(a) administering orally to the individual a composition comprising *Bacillus subtilis* in a dose of from about $1 \cdot 10^8$ CFU per day to about $1 \cdot 10^{11}$ CFU per day for at least 15 days;

wherein the frequency of the individual's 24-hour episodes per month of bowel movements measuring 6 or 7 on the Bristol Stool Scale does not increase during the at least 15 days of administration.

The method described herein effects maintenance of gastrointestinal regularity in an individual.

In yet another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 15 days;

wherein the frequency of the individual's 24-hour episodes per month of bowel movements measuring 6 or 7 on the Bristol Stool Scale does not increase during the at least 15 days of administration.

The method described herein effects maintenance of gastrointestinal regularity in an individual.

In yet another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 30 days;

wherein the frequency of the individual's 24-hour episodes per month of bowel movements measuring 6 or 7 on the Bristol Stool Scale does not increase during the at least 30 days of administration.

The method described herein effects maintenance of gastrointestinal regularity in an individual.

In yet another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 60 days;

wherein the frequency of the individual's 24-hour episodes per month of bowel movements measuring 6 or 7 on the Bristol Stool Scale does not increase during the at least 60 days of administration.

The method described herein effects maintenance of gastrointestinal regularity in an individual.

In yet another embodiment, a method of maintaining gastrointestinal regularity in an individual can include the steps of:

(a) administering orally to the individual a composition comprising *Bacillus subtilis* in a dose of about $1 \cdot 10^9$ CFU per day for at least 90 days;

wherein the frequency of the individual's 24-hour episodes per month of bowel movements measuring 6 or 7 on the Bristol Stool Scale does not increase during the at least 90 days of administration.

The method described herein effects maintenance of gastrointestinal regularity in an individual.

In an embodiment, a method of promoting gastrointestinal regularity in an individual can include the steps of:

(a) administering orally to the individual a composition comprising *Bacillus subtilis* in a dose of from about 1·10$^8$ CFU per day to about 1·10$^{11}$ CFU per day for at least 15 days;

wherein the frequency of the individual's 24-hour periods of bowel movements measuring from 3 to 5 on the Bristol Stool Scale increases.

The method described herein effects promotion of gastrointestinal regularity in an individual.

In another embodiment, a method of promoting gastrointestinal regularity in an individual can include the steps of:

(a) administering orally to the individual a composition comprising *Bacillus subtilis* in a dose of about 1·10$^9$ CFU per day for at least 15 days;

wherein the frequency of the individual's 24-hour periods of bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of about 1·10$^9$ CFU per day for at least 30 days;

wherein the frequency of the individual's 24-hour periods of bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of about 1·10$^9$ CFU per day for at least 60 days;

wherein the frequency of the individual's 24-hour periods of bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of about 1·10$^9$ CFU per day for at least 90 days;

wherein the frequency of the individual's 24-hour periods of bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of from about 1·10$^8$ CFU per day to about 1·10$^{11}$ CFU per day for at least 15 days;

(b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of about 1·10$^9$ CFU per day for at least 15 days;

(b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of about 1·10$^9$ CFU per day for at least 30 days;

(b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of about 1·10$^9$ CFU per day for at least 60 days;

(b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

The method described herein effects promotion of gastrointestinal regularity in an individual.

In yet another embodiment, a method of promoting gastrointestinal regularity in an individual can include the steps of:

(a) administering orally to the individual a composition comprising *Bacillus subtilis* in a dose of about 1·10$^9$ CFU per day for at least 90 days;

(b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

The method described herein effects promotion of gastrointestinal regularity in an individual.

In an embodiment, a method of restoring gastrointestinal regularity in an individual, wherein the individual has at least one 24-hour episode per month of bowel movements measuring 1 or 2 on the Bristol Stool Scale, can include the steps of:

(a) administering orally to the individual a composition comprising *Bacillus subtilis* in a dose of from about 1·10$^8$ CFU per day to about 1·10$^{11}$ CFU per day for at least 15 days;

wherein the frequency of 24-hour periods of the individual's bowel movements measuring from 3 to 5 on the Bristol Stool Scale increases.

The method described herein effects restoration of gastrointestinal regularity in an individual.

In another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 15 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 30 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 60 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 90 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days;
  (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 15 days;
  (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 30 days;
  (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 60 days;
  (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 1 or 2 on the Bristol Stool Scale, can include the steps of:
  (a) administering orally to the individual a composition comprising *Bacillus subtilis* in a dose of about $1 \cdot 10^9$ CFU per day for at least 90 days;
  (b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of about $1 \cdot 10^9$ CFU per day for at least 15 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of about $1 \cdot 10^9$ CFU per day for at least 30 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of about $1 \cdot 10^9$ CFU per day for at least 60 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of about $1 \cdot 10^9$ CFU per day for at least 90 days;
  wherein the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of from about $1 \cdot 10^8$ CFU per day to about $1 \cdot 10^{11}$ CFU per day for at least 15 days;
  (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of about $1 \cdot 10^9$ CFU per day for at least 15 days;
  (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of about $1 \cdot 10^9$ CFU per day for at least 30 days;
  (b) measuring the individual's bowel movements according to the Bristol Stool Scale;
  wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
  (a) administering orally to the individual a composition comprising *Bacillus subtilis* in a dose of about $1 \cdot 10^9$ CFU per day for at least 60 days;
  (b) measuring the individual's bowel movements according to the Bristol Stool Scale;

wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In yet another embodiment, a method of restoring gastrointestinal regularity in an individual, wherein the individual has at least one 24-hour episode per month of bowel movements measuring 6 or 7 on the Bristol Stool Scale, can include the steps of:
(a) administering orally to the individual a composition comprising *Bacillus subtilis* in a dose of about $1 \cdot 10^9$ CFU per day for at least 90 days;
(b) measuring the individual's bowel movements according to the Bristol Stool Scale;
wherein steps (a) and (b) are repeated at least until the frequency of 24-hour periods of the individual's bowel movements measuring from 3 to 5 on the Bristol Stool Scale increases.

The method described herein effects restoration of gastrointestinal regularity in an individual.

In an embodiment, a method of maintaining healthy gut microflora in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 15 days;
wherein the frequency of the individual's 24-hour episodes per month of bowel movements measuring from 3 to 5 on the Bristol Stool Scale does not decrease during the at least 15 days of administration.

The method described herein effects maintenance of healthy gut microflora in an individual.

In another embodiment, a method of maintaining healthy gut microflora in an individual can include the steps of:
(a) administering orally to the individual a composition comprising *Bacillus subtilis* in a dose of about $1 \cdot 10^9$ CFU per day for at least 15 days;
wherein the frequency of the individual's 24-hour episodes per month of bowel movements measuring from 3 to 5 on the Bristol Stool Scale does not increase during the at least 15 days of administration.

The method described herein effects maintenance of healthy gut microflora in an individual.

In yet another embodiment, a method of maintaining healthy gut microflora in an individual can include the steps of:
(a) administering orally to the individual a composition comprising *Bacillus subtilis* in a dose of about $1 \cdot 10^9$ CFU per day for at least 30 days;
wherein the frequency of the individual's 24-hour episodes per month of bowel movements measuring from 3 to 5 on the Bristol Stool Scale does not increase during the at least 30 days of administration.

The method described herein effects maintenance of healthy gut microflora in an individual.

In yet another embodiment, a method of maintaining healthy gut microflora in an individual can include the steps of:
(a) administering orally to the individual a composition comprising *Bacillus subtilis* in a dose of about $1 \cdot 10^9$ CFU per day for at least 60 days;
wherein the frequency of the individual's 24-hour episodes per month of bowel movements measuring from 3 to 5 on the Bristol Stool Scale does not increase during the at least 60 days of administration.

The method described herein effects maintenance of healthy gut microflora in an individual.

In yet another embodiment, a method of maintaining healthy gut microflora in an individual can include the steps of:
(a) administering orally to the individual a composition comprising *Bacillus subtilis* in a dose of about $1 \cdot 10^9$ CFU per day for at least 90 days;
wherein the frequency of the individual's 24-hour episodes per month of bowel movements measuring from 3 to 5 on the Bristol Stool Scale does not increase during the at least 90 days of administration.

The method described herein effects maintenance of healthy gut microflora in an individual.

In certain embodiments, the compositions comprising *Bacillus subtilis* can include one or more dry carriers selected from the group consisting of trehalose, maltodextrin, rice flour, microcrystalline cellulose, magnesium stearate, inositol, fructooligosaccharide, galactooligosaccharide, dextrose, and the like. In certain embodiments, the dry carrier can be added to the compositions comprising *Bacillus subtilis* in a weight percentage of from about 1% to about 95% by weight of the composition.

In certain embodiments, the compositions comprising *Bacillus subtilis* can include one or more liquid or gel-based carriers, selected from the group consisting of water and physiological salt solutions, urea, alcohols and derivatives thereof (e.g., methanol, ethanol, propanol, butanol), glycols (e.g., ethylene glycol, propylene glycol), and the like; natural or synthetic flavorings and food-quality coloring agents, all compatible with the organism; thickening agents selected from the group consisting of corn starch, guar gum, xanthan gum, and the like; one or more spore germination inhibitors selected from the group consisting of hyper-saline carriers, methylparaben, guargum, polysorbate, preservatives, and the like. In certain embodiments, the one or more liquid or gel-based carrier(s) can be added to the compositions comprising *Bacillus subtilis* in a weight/volume percentage of from about 0.6% to about 95% weight/volume of the composition. In certain embodiments, the natural or synthetic flavoring(s) can be added to the compositions comprising *Bacillus subtilis* in a weight/volume percentage of from about 3.0% to about 10.0% weight/volume of the composition. In certain embodiments, the coloring agent(s) can be added to the compositions comprising *Bacillus subtilis* in a weight/volume percentage of from about 1.0% to about 10.0% weight/volume of the composition. In certain embodiments, the thickening agent(s) can be added to the compositions comprising *Bacillus subtilis* in a weight/volume percentage of about 2% weight/volume of the composition. In certain embodiments, the one or more spore germination inhibitors can be added to the compositions comprising *Bacillus subtilis* in a weight/volume percentage of about 1% weight/volume of the composition.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films, or oral dissolvable strips can be used. Other useful delivery systems comprise oral or nasal sprays or inhalers, and the like.

For oral administration, probiotics may be further combined with one or more solid inactive ingredients for the preparation of tablets, capsules, pills, powders, granules, or other suitable dosage forms. For example, the active agent may be combined with at least one excipient selected from the group consisting of fillers, binders, humectants, disintegrating agents, solution retarders, absorption accelerators, wetting agents, absorbents, and lubricating agents. Other useful excipients include, but are not limited to, magnesium stearate, calcium stearate, mannitol, xylitol, sweeteners, starch, carboxymethylcellulose, microcrystalline cellulose, silica, gelatin, silicon dioxide, and the like.

In certain embodiments, the components of compositions administered according to the methods of the present disclosure, together with one or more conventional adjuvants, carriers, or diluents, may thus be placed into the form of pharmaceutical compositions and unit dosages thereof. Such forms include: solids, and in particular, tablets, filled capsules, powder and pellet forms; liquids, and in particular, aqueous or non-aqueous solutions, suspensions, emulsions, elixirs; and capsules filled with the same; all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The components of the compositions administered according to the methods of the present disclosure can be administered in a wide variety of oral and parenteral dosage forms. It will be obvious to those skilled in the art that the following dosage forms may comprise, in certain embodiments, as the active component, either a chemical compound of the present disclosure or a pharmaceutically acceptable salt of a chemical compound of the present disclosure.

For preparing pharmaceutical compositions to be administered according to the methods of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or encapsulating materials.

In powders, the carrier is a finely divided solid, which is in a mixture with the finely divided active component. In tablets, the active component is mixed with the carrier having the necessary binding capacity in suitable proportions and compacted in the shape and size desired.

In certain embodiments, powders and tablets administered according to methods of the present disclosure preferably may contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without additional carriers, is surrounded by a carrier, which is thus in association with it. Similarly, cachets and lozenges are included. Tablets, powders, capsules, pills, cachets, and lozenges are included. Tablets, powders, capsules, pills, cachets, and lozenges can be used as solid forms suitable for oral administration.

Liquid preparations include, but are not limited to, solutions, suspensions, and emulsions, for example, water or water-propylene glycol solutions. For example, parenteral injection liquid preparations can be formulated as solutions in aqueous polyethylene glycol solution. In certain embodiments, chemical compounds administered according to methods of the present disclosure may thus be formulated for parenteral administration (e.g., by injection, for example, bolus injection or continuous infusion) and may be presented in unit dose for administration in ampoules, pre-filled syringes, small-volume infusion, or in multi-dose containers with an added preservative. The compositions may take such forms as suspensions, solutions, or emulsions in oily or aqueous vehicles, and may contain formulation agents such as suspending, stabilizing, and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Compositions suitable for topical administration in the mouth include, but are not limited to: lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example, with a dropper, pipette, or spray. The compositions may be provided in single or multi-dose form. In compositions intended for administration to the respiratory tract, including intranasal compositions, the compound will generally have a small particle size, for example, of the order of 5 microns or less. Such a particle size may be obtained by means known in the art, for example, by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself; or it can be the appropriate number of any of these in packaged form.

Tablets, capsules, and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of REMINGTON'S PHARMACEUTICAL SCIENCES (Mack Publishing Co., Easton, PA).

Routes of Administration

The compounds may be administered by any route, including, but not limited to, oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection, or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in the form of shaped articles, e.g. films or microcapsules.

The methods described above may be further understood in connection with the following Examples. In addition, the following non-limiting examples are provided to illustrate the invention. However, the person skilled in the art will appreciate that it may be necessary to vary the procedures for any given embodiment of the invention, e.g., vary the order or steps.

EXAMPLE 1

*Bacillus subtilis Bacillus subtilis* probiotics have been shown to influence several aspects of the human gut including motility, epithelial strength, inflammation, etc. that may change bowel movement frequency and/or type. To explore the efficacy of *Bacillus subtilis* ("*B. subtilis*") DE111® (*Bacillus subtilis* subspecies *inaquosorum* having Accession No. NRRL B-67989) in this regard, 50 people were evaluated by their stool profile, food diary, and questionnaire, while taking a probiotic or placebo daily, over the course of 105 days. The stools were scored based on the Bristol Stool Chart index. Statistically significant results showed that participants in the *Bacillus subtilis* DE111® group moved to a healthier bowel index, while participants in the placebo group remained at the same bowel index, providing evidence that *Bacillus subtilis* DE111® may improve occasional constipation and/or diarrhea.

The purpose of this double-blind, randomized study was to determine the efficacy of *Bacillus subtilis* DE111® (*Bacillus subtilis* subspecies *inaquosorum* having Accession No. NRRL B-67989) in capsule form for regulation of bowel movements. 50 adults (18-65 years of age at the time of participation) suffering from occasional constipation and/or diarrhea were assigned to consume either $1 \cdot 10^9$ CFU of *Bacillus subtilis* DE111® or placebo. Each group was instructed to consume one capsule per day, with a meal, for 90 days. Efficacy was assessed through participant-reported bowel movement ("BM") records as well as dietary intake logs.

I. Materials and Methods
A. Composition of Supplement and Placebo

Each *Bacillus subtilis* DE111® (*Bacillus subtilis* subspecies *inaquosorum* having Accession No. NRRL B-67989) supplement ("Capsule A") contained a dose of $1 \cdot 10^9$ CFU of *Bacillus subtilis* DE111® diluted to concentration with low-moisture rice dextrin. Placebo supplements ("Capsule B") contained only low-moisture rice dextrin. Both *Bacillus subtilis* DE111® and placebo were encapsulated in size one opaque vegetable capsules.

B. Subject Recruitment

Participant recruitment included online postings to Clinical Connection, Atlanta Job Exchange, and social media for local interest sites. Furthermore, recruitment flyers were posted throughout the metropolitan Atlanta area.

C. Participant Demographics and Inclusion Criteria

This study aimed to use a diverse participant population representative of the general population. 50 adults, ages 18-65 at time of participation, and suffering from occasional constipation and/or diarrhea, completed this study. Initially, 65 individuals were enrolled, but 7 individuals were dropped due to their initial bloodwork results, 6 individuals were dropped due to CRP levels higher than 5 mg/L, and 2 individuals opted out mid-study. Occasional constipation/diarrhea was defined as frequency ranging from 1-5 episodes per month, with each episode lasting a minimum of 24 hours. Medical history questionnaires, digestive health questionnaires, and initial blood samples were collected and assessed by a board-certified physician to determine the general health of participants before complete inclusion. Blood samples were also collected at days 45 and 105, and health questionnaires were completed on days 1, 15, 45, 75, and 105. Blood samples were collected at LabCorp locations that were convenient to each participant. C-reactive protein ("CRP"), lipid panels, and complete metabolic panel ("CMP") levels were used as a safety screen to determine participant health at time of inclusion. Trained phlebotomists used routine venipuncture procedures to collect blood samples from participants.

D. Data Collection Procedures

Participants recorded daily entries of their dietary intake and bowel movement ("BM") records throughout the 90 days. The daily BM logs required participants to score their bowel movements using the Bristol Stool chart. Additionally, digestive health questionnaires were completed on days 1, 15, 45, 75 and 105 using the online survey service Survey Monkey. The questionnaires required participants to rate their general digestive health by the following scale: 0=symptom is not present; 1=mild/sometimes; 2=moderate/often; and 3=severe/almost always. Participants had the option to use controlled electronic documents or hard copy packets to complete the daily BM logs and digestive health questionnaires.

E. Incentives, Follow-Ups, Compensation

Participants could withdraw from the study at any time without penalty. Daily interaction encouraged participants to maintain daily tasks, ask questions, and voice concerns. Communication included email and phone calls to remind participants of upcoming questionnaires and sample collections. Participants who completed the study were paid an honorarium in appreciation for their time.

F. Statistical Analysis

The participants were tested for differences between the *Bacillus subtilis* DE111® (*Bacillus subtilis* subspecies *inaquosorum* having Accession No. NRRL B-67989) and the Placebo groups as well as differences within groups. The subgroups included gender (female vs. male) and age (under 30 (n=28) and over 30 (n=22)), to preserve a larger sample size and balance proportion between groups. See Table 1.

The Bristol stool types describe various states of bowel transit health, including: hard to pass stools, constipated (Bristol 1-2); normal (Bristol 3-5); and very loose stools, diarrhea (Bristol 6-7). This scale was regrouped into a ranking scale: 1 (Bristol 1 and 7, the worst scale numbers for diarrhea and constipation); 2 (Bristol 2 and 6); 3 (Bristol 5); and ideal 4 (Bristol 3 and 4). Collectively, these were referred to as "BM Transit Health."

Bristol types were placed into a binary categorical group consisting of "Normal" (Bristol 3, 4, and 5) and "Non-normal" stools (Bristol 1, 2, 6, and 7). The data on BM state was divided into six 15-day intervals. Interval 1 (days 1-15), Interval 2 (days 16-30), Interval 3 (days 31-45), Interval 4 (days 46-60), Interval 5 (days 61-75), and Interval 6 (days 76-90). All time groups were tested for independence in proportions using the Chi-Square test statistic.

The proportions between groups and the change in proportions from interval 1 to interval 6 within each group was tested using Chi-squared tests for the BM State variable of "Normal" and "Non-normal" stools. All the hypotheses-based tests of proportions were two-sided and statistical significance was accepted at the p=0.05 level. No adjustments for multiple comparisons were made. The questionnaires were analyzed using a paired sample T-Test comparing group scores.

Independent t-tests were used for between-group differences with respect to capsule type, and paired t-tests were used to assess within group differences with respect to time. Between-group differences with respect to capsule type are reported. Independent sample T-tests were used to test for differences between Capsule A and Capsule B at each point of the study: baseline, mid, and final. Paired sample T-tests were used to assess the differences between Capsule A at baseline, mid-point, and post-study; and for Capsule B at each point in the study. P-values below 0.05 were considered significant, and p-values between 0.05-0.10 were considered near-significant.

All statistical analysis was completed using the R language and environment for statistical computing (version 3.3.2, R Foundation for Statistical Computing, Vienna, Austria).

Figure 2:
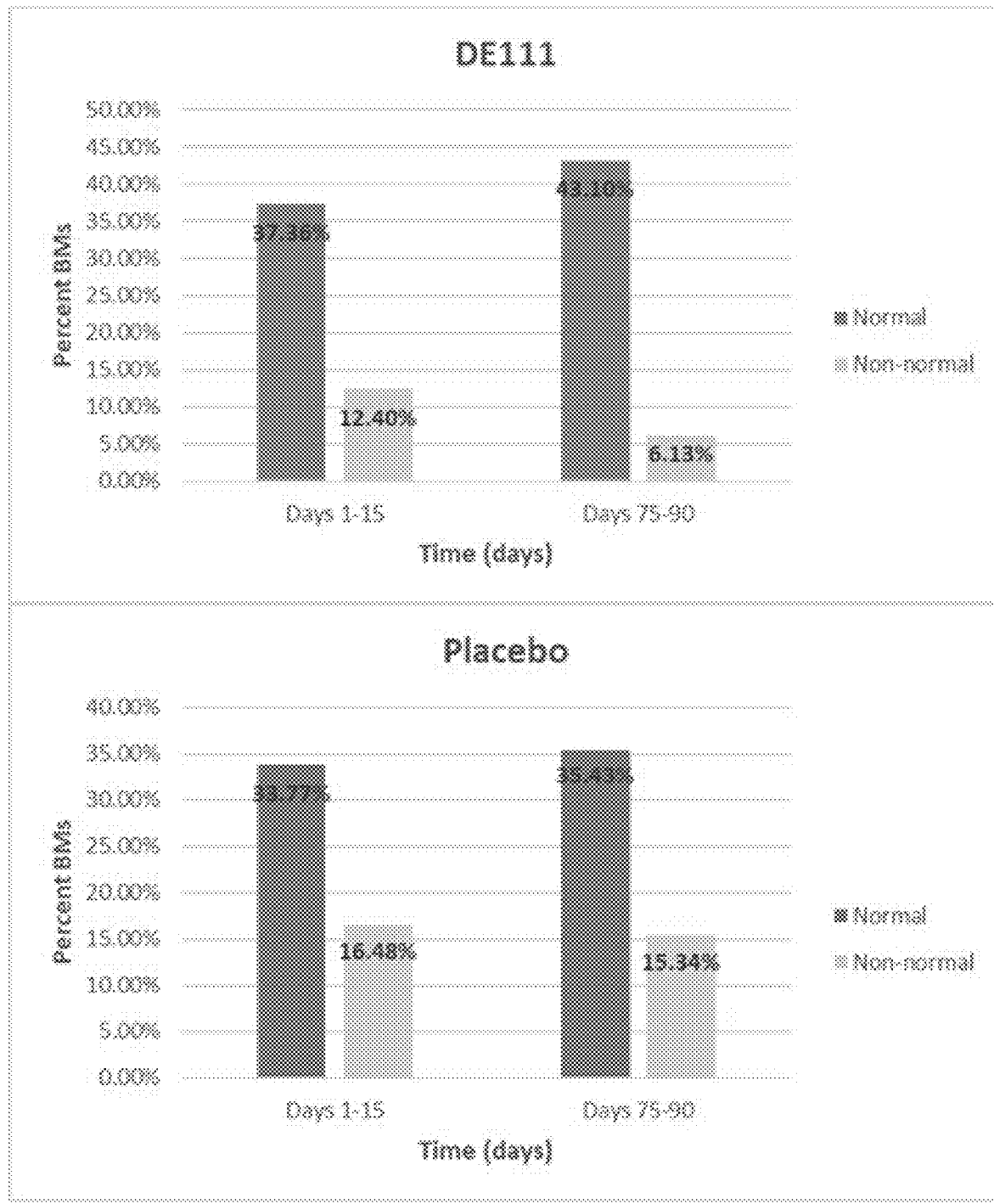
FIG. 2 depicts the percentages of Normal and Non-normal BMs in study participants administered Bacillus subtilis DE111® (Bacillus subtilis subspecies inaquosorum having Accession No. NRRL B-67989) (top panel) and study participants administered placebo (bottom panel).

The results of the Chi-Square test indicated that over time, and, by Interval 6, the strength of the difference in proportions of Normal vs. Non-normal stool types increased for the probiotic group (See FIG. 2).

Comprehensive metabolic panels and lipid panels stayed within normal reference ranges both in the probiotic and placebo groups with no adverse effects or significant serum level differences. CRP levels remained within normal levels for both probiotic and placebo groups throughout the study.

The difference in means between Interval 1 and Interval 6 for the Bacillus subtilis DE111® (Bacillus subtilis subspecies inaquosorum having Accession No. NRRL B-67989) are statistically significant. By day 90, the proportion of Normal stools (43.1%) to Non-normal stools (6.13%) in the Bacillus subtilis DE111® group differed significantly (p=5.866E-08; Chi-squared 29.407) from that in the Placebo group (See FIGS. 2 and 3, and Table 3). The proportion of normal Bristol stools type 3 and 4 increased from 37.36% in week 1 to 43.1% in the last week of the study. The proportions of Normal stools in the Placebo group stayed roughly the same from 33.77% to 35.47%; the degree of change was insignificant and not attributable to any other factor in the research (p=0.137; Chi-squared 2.204). By days 75-90, there is a significant increase in Normal stool types of participants in the Bacillus subtilis DE111® group. Significant increase in Normal stool types of participants in the placebo group was not observed, and in fact, a decrease in Normal stools was observed.

Results of the questionnaires completed were analyzed. Paired sample t-tests of groups showed a reduction in the mean score for the question, "Have you experienced alternating constipation and diarrhea?" (0=symptom is not present, 1=symptom is sometimes present, 2=symptom is often present, 3=symptom is almost always present) from a day 1 mean of 0.42 down to a day 15 mean of 0.11 (p=0.05). No other statistically meaningful differences between the Bacillus subtilis DE111® (Bacillus subtilis subspecies inaquosorum having Accession No. NRRL B-67989) and Placebo groups, or between questions, were found.

TABLE 1

Participant Characteristics

| Demographic | Statistic | Probiotic (A) (N = 24) | Placebo (B) (N = 26) | Females (N = 36) | Males (N = 14) | Under 30 (N = 28) | Over 30 (N = 22) | Overall (N = 50) |
|---|---|---|---|---|---|---|---|---|
| Age | Mean | 30.1 | 32.9 | 31.5 | 31.9 | 23.3 | 42.6 | 31.6 |
|  | Min-Max | 19-53 | 22-64 | 19-64 | 20-53 | 19-29 | 30-64 | 19-64 |
| Bristol Type | Mean | 3.48 | 3.36 | 3.44 | 3.37 | 3.45 | 3.37 | 3.42 |
|  | Min-Max | 1-7 | 1-7 | 1-7 | 1-7 | 1-7 | 1-7 | 1-7 |
| *Transit health | Mean | 3.29 | 3.12 | 3.20 | 3.18 | 3.23 | 3.15 | 3.20 |
|  | Min-Max | 1-4 | 1-4 | 1-4 | 1-4 | 1-4 | 1-4 | 1-4 |

*BM health was scaled from the self-reported Bristol Stool types: 1 = Very Poor; 2 = Poor; 3 = Fair; 4 = Good.

II. Results

The mean BM Transit Health was significantly different in days 75-90 (final two weeks) vs. the first two weeks among the Capsule A group (p-value=0.0369) moving from non-healthy stools to healthy stools. There were no strong differences found when other ranges of days were compared in the placebo group (Table 2).

TABLE 2

Mean BM Transit health for Days 1-15 vs. Days 75-90

|  |  | Day 1-15 | Day 75-90 | P-value |
|---|---|---|---|---|
| Capsule A | Mean | 3.29 | 3.45 | 0.0369 |
| Capsule B | Mean | 3.06 | 3.08 | 0.7386 |

TABLE 3

BM State compared by Capsule Group and Time

|  | Interval | A | B | Group Total | Chi Square | p-value |
|---|---|---|---|---|---|---|
| Non-Normal | 1 | 76 | 101 | 177 | 4.2511 | 0.3922 |
| Normal |  | 229 | 207 | 436 |  |  |
| Non-Normal | 2 | 68 | 105 | 173 | 9.0109 | 0.002684 |
| Normal |  | 235 | 207 | 442 |  |  |
| Non-Normal | 3 | 64 | 85 | 149 | 2.6626 | 0.1027 |
| Normal |  | 237 | 227 | 464 |  |  |
| Non-normal | 4 | 70 | 97 | 167 | 3.4943 | 0.06158 |
| Normal |  | 235 | 228 | 463 |  |  |
| Non-normal | 5 | 71 | 111 | 182 | 9.7593 | 0.001784 |
| Normal |  | 238 | 210 | 448 |  |  |
| Non-normal | 6 | 40 | 100 | 140 | 29.407 | 5.866E−08 |
| Normal |  | 281 | 231 | 512 |  |  |

III. Discussions

Bacteria make up more than 50% of the composition of a healthy person's stool and play a major role in the quality and frequency of bowel movements. Probiotics are live microorganisms that confer a gastrointestinal health benefit to the host. Gastrointestinal regularity may be the result of several potential probiotic mechanisms of action. The presence of probiotics may modify the gastrointestinal microbiota. Probiotics may release metabolites that can alter gut function, including satiety and motility. Some probiotics can increase the production of lactate and short-chain fatty acids, reducing luminal pH, which has been proposed to enhance gut transit time and reduce inflammation.

Bacillus subtilis DE111® (Bacillus subtilis subspecies inaquosorum having Accession No. NRRL B-67989) significantly improved gastrointestinal discomfort including constipation and diarrhea over the course of the study. Individuals in the Bacillus subtilis DE111® group reported an increased frequency of normal type stools compared to those in the placebo group. Therefore, a Bacillus subtilis DE111® dose at 1 billion CFU/day may improve occasional constipation and diarrhea while helping to maintain gastrointestinal health.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof, and, accordingly, reference should be made to the appended claims, rather than to the foregoing specification, as indicating the scope of the invention.

We claim:

1. A method of treating gastrointestinal irregularity in an individual, wherein the individual has at least one 24-hour episode per month of bowel movements measuring 1 or 2 on the Bristol Stool Scale, comprising:
   (a) administering orally to the individual a composition consisting essentially of an isolated strain of Bacillus subtilis subspecies inaquosorum having accession number NRRL B-67989 in a dose of from $1 \times 10^8$ CFU per day to $1 \times 10^{11}$ CFU per day for at least 15 days,
   wherein the frequency of the individual's 24-hour episodes per month of bowel movements measuring 1 or 2 on the Bristol Stool Scale decreases.

2. The method of claim 1, wherein the administering step is performed for at least 30 days.

3. The method of claim 1, wherein the administering step is performed for at least 60 days.

4. The method of claim 1, wherein the administering step is performed for at least 90 days.

5. The method of claim 1, wherein the composition consists essentially of Bacillus subtilis subspecies inaquosorum having accession number NRRL B-67989 in a dose of $1 \times 10^9$ CFU per day.

6. The method of claim 1, further comprising the step of:
   (b) measuring the individual's bowel movements according to the Bristol Stool Scale,
   wherein steps (a) and (b) are repeated at least until the frequency of the individual's 24-hour episodes per month of bowel movements measuring 1 or 2 on the Bristol Stool Scale decreases.

7. A method of treating gastrointestinal irregularity in an individual, wherein the individual has at least one 24-hour episode per month of bowel movements measuring 6 or 7 on the Bristol Stool Scale, comprising:
   (a) administering orally to the individual a composition consisting essentially of Bacillus subtilis subspecies inaquosorum having accession number NRRL B-67989 in a dose of from $1 \times 10^8$ CFU per day to $1 \times 10^{11}$ CFU per day for at least 15 days,
   wherein the frequency of the individual's 24-hour episodes per month of bowel movements measuring 6 or 7 on the Bristol Stool Scale decreases.

8. The method of claim 7, wherein the administering step is performed for at least 30 days.

9. The method of claim 7, wherein the administering step is performed for at least 60 days.

10. The method of claim 7, wherein the administering step is performed for at least 90 days.

11. The method of claim 7, wherein the composition consists essentially of *Bacillus subtilis* subspecies *inaquosorum* having accession number NRRL B-67989 in a dose of $1\times10^9$ CFU per day.

12. The method of claim 7, further comprising the step of: (b) measuring the individual's bowel movements according to the Bristol Stool Scale, wherein steps (a) and (b) are repeated at least until the frequency of the individual's 24-hour episodes per month of bowel movements measuring 6 or 7 on the Bristol Stool Scale decreases.

13. A method of maintaining gastrointestinal regularity in an individual, comprising:
(a) administering orally to the individual a composition consisting essentially of *Bacillus subtilis* subspecies *inaquosorum* having accession number NRRL B-67989 in a dose of from $1\times10^8$ CFU per day to $1\times10^{11}$ CFU per day for at least 15 days,
wherein the frequency of the individual's 24-hour episodes per month of bowel movements measuring 1 or 2 or 6 or 7 on the Bristol Stool Scale does not increase during the at least 15 days.

14. The method of claim 13, wherein the administering step is performed for at least 30 days.

15. The method of claim 13, wherein the administering step is performed for at least 60 days.

16. The method of claim 13, wherein the administering step is performed for at least 90 days.

17. The method of claim 13, wherein the composition consists essentially of *Bacillus subtilis* subspecies *inaquosorum* having accession number NRRL B-67989 in a dose of $1\times10^9$ CFU per day.

18. The method of claim 13 for promoting gastrointestinal regularity in an individual, wherein the frequency of the individual's 24-hour periods of bowel movements measuring from 3 to 5 on the Bristol Stool Scale increases.

19. The method of claim 18, wherein the administering step is performed for at least 30 days.

20. The method of claim 18, wherein the administering step is performed for at least 60 days.

21. The method of claim 18, wherein the administering step is performed for at least 90 days.

22. The method of claim 18, wherein the composition consists essentially of *Bacillus subtilis* subspecies *inaquosorum* having accession number NRRL B-67989 in a dose of $1\times10^9$ CFU per day.

23. The method of claim 18, further comprising the step of:
(b) measuring the individual's bowel movements according to the Bristol Stool Scale,
wherein steps (a) and (b) are repeated at least until the frequency of 24-hour periods of the individual's bowel movements measuring from 3 to 5 on the Bristol Stool Scale increases.

24. A method of restoring gastrointestinal regularity in an individual, wherein the individual has at least one 24-hour episode per month of bowel movements measuring 1 or 2 or 6 or 7 on the Bristol Stool Scale, comprising:
(a) administering orally to the individual a composition consisting essentially of *Bacillus subtilis* subspecies *inaquosorum* having accession number NRRL B-67989 in a dose of from $1\times10^8$ CFU per day to $1\times10^{11}$ CFU per day for at least 15 days,
wherein the frequency of 24-hour periods of the individual's bowel movements measuring from 3 to 5 on the Bristol Stool Scale increases.

25. The method of claim 24, wherein the administering step is performed for at least 30 days.

26. The method of claim 24, wherein the administering step is performed for at least 60 days.

27. The method of claim 24, wherein the administering step is performed for at least 90 days.

28. The method of claim 24, wherein the composition consists essentially of *Bacillus subtilis* subspecies *inaquosorum* having accession number NRRL B-67989 in a dose of $1\times10^9$ CFU per day.

29. The method of claim 24, further comprising the step of: (b) measuring the individual's bowel movements according to the Bristol Stool Scale,
wherein steps (a) and (b) are repeated at least until the frequency of 24-hour periods of the individual's bowel movements measuring from 3 to 5 on the Bristol Stool Scale increases.

\* \* \* \* \*